United States Patent [19]

Roberts et al.

[11] Patent Number: 5,958,791
[45] Date of Patent: *Sep. 28, 1999

[54] INTERDIGITATED ELECTRODE ARRAYS FOR LIPOSOME-ENHANCED IMMUNOASSAY AND TEST DEVICE

[75] Inventors: Matthew A Roberts, Bussigny, Switzerland; Richard Allen Durst, Romulos, N.Y.; Richard A. Montagna, Grand Island, N.Y.; Geoffrey S. Rule, Geneva, N.Y.

[73] Assignee: Innovative Biotechnologies, Inc., Niagara Falls, N.Y.

[ * ] Notice: This patent issued on a continued prosecution application filed under 37 CFR 1.53(d), and is subject to the twenty year patent term provisions of 35 U.S.C. 154(a)(2).

[21] Appl. No.: 08/722,901

[22] Filed: Sep. 27, 1996

[51] Int. Cl.$^6$ .................................................. G01N 33/533
[52] U.S. Cl. ........................... 436/514; 422/56; 422/57; 422/70; 422/82.01; 422/82.03; 422/98; 422/99; 422/110; 427/213.3; 427/213.34; 427/213.35; 436/516; 436/518; 436/530; 436/541; 435/3; 435/7.1; 435/7.93; 435/287.7; 435/970; 204/182.7; 204/286; 204/288; 204/290
[58] Field of Search ................................. 422/56, 57, 70, 422/82.01, 82.03, 98, 99, 110; 427/213.3, 213.34, 213.35; 435/3, 7.1, 7.93, 287.7, 970; 436/516, 518, 530, 541; 204/182.7, 286, 288, 290 R, 297 R

[56] References Cited

U.S. PATENT DOCUMENTS

| | | |
|---|---|---|
| 4,235,601 | 11/1980 | Deutsch et al. . |
| 4,806,311 | 2/1989 | Greenquist . |
| 4,822,566 | 4/1989 | Newman . |
| 5,001,048 | 3/1991 | Taylor et al. . |
| 5,006,473 | 4/1991 | Bouma et al. . |
| 5,045,285 | 9/1991 | Kolesar, Jr. . |
| 5,096,629 | 3/1992 | Nanba et al. . |
| 5,130,257 | 7/1992 | Baer et al. . |
| 5,141,868 | 8/1992 | Shanks et al. . |
| 5,200,051 | 4/1993 | Cozzette et al. . |
| 5,308,775 | 5/1994 | Donovan et al. . |
| 5,312,762 | 5/1994 | Guiseppi-Elie . |

FOREIGN PATENT DOCUMENTS 2 204 398  11/1988  United Kingdom .

OTHER PUBLICATIONS

Durst et al., Development of Liposome–Enhanced Immuno–Biosensing Devices for Field Measurements of Toxic Substances. 2nd Bioelectroanalytical Symposium., 1992.

Niwa et al., "Electrochemical Behavior of Reversible Redox Species at Interdigitated Array Electrodes with Different Geometrics: Consideration of Redox Cycling and Collection Efficiency," *Anal. Chem.* , 62:447–452 (1990).

Niwa et al., "Small–Volume Voltammetric Detection of 4–Aminophenol with Interdigitated Array Electrodes and Its Application to Electrochemical Enzyme Immunoassay," *Anal. Chem.* , 65:1559–1563 (1993).

*Primary Examiner*—Christopher L. Chin
*Assistant Examiner*—Bao-Thuy L. Nguyen
*Attorney, Agent, or Firm*—Nixon, Hargrave, Devans & Doyle LLP

[57] ABSTRACT

A test device for detecting or determining an analyte in a test solution includes an absorbent material having contact, liposome lysing and electrochemical measurement portions. The contact portion is positioned for contact with and uptake of the test solution. The liposome lysing portion is segregated from the contact portion and has a liposome lysing agent bound thereto. The liposome lysing portion is further either positioned between the contact portion and the electrochemical measurement portion, or partially or completely coincides with the electrochemical measurement portion. The electrochemical measurement portion comprises a first conductor comprising a plurality of fingers disposed on the absorbent material, and a second conductor similarly comprising a plurality of fingers disposed on the absorbent material, where the fingers of the first and second conductors are interdigitated to form an array.

43 Claims, 6 Drawing Sheets

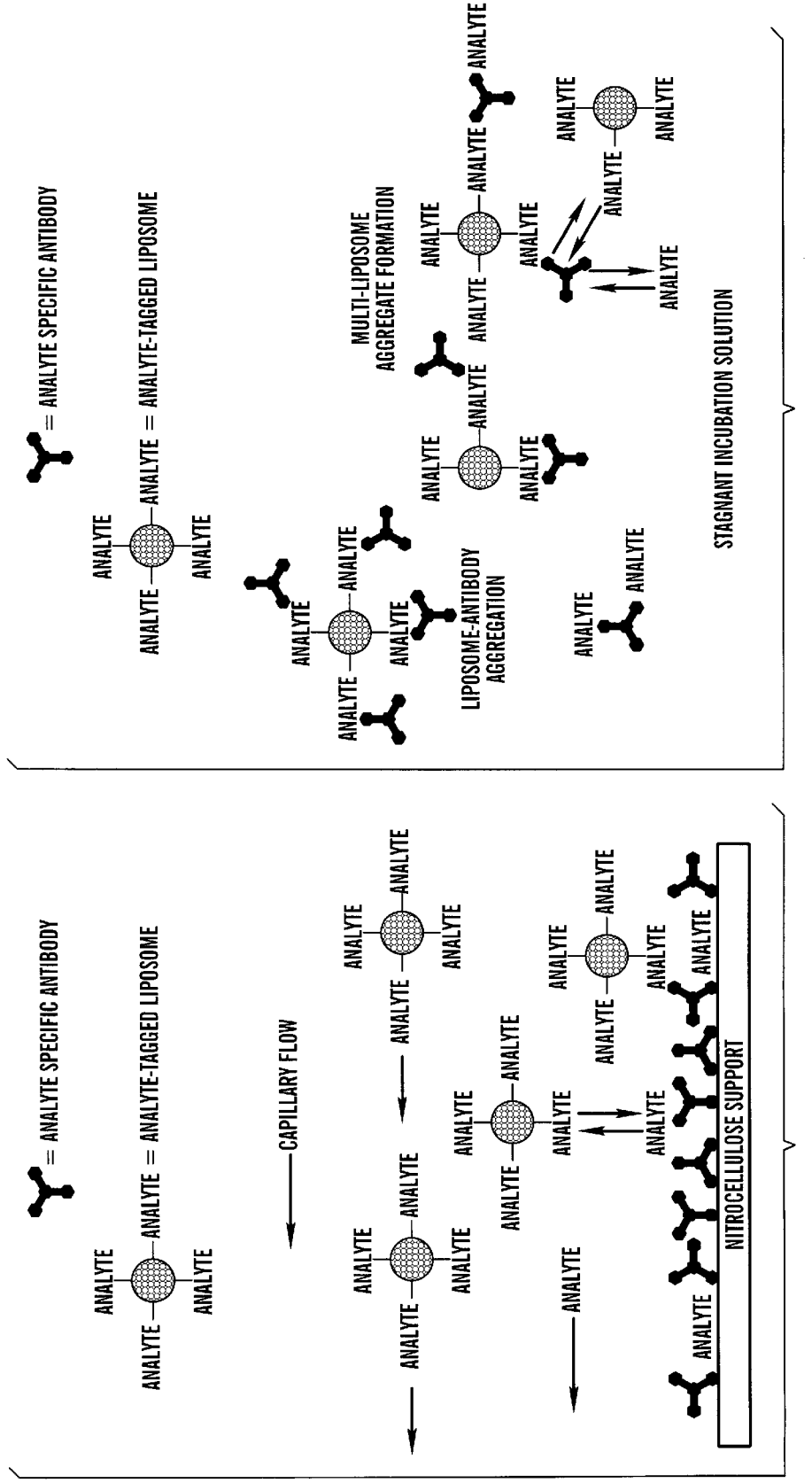

INTERDIGITATED ELECTRODE ARRAYS FOR LIPOSOME-ENHANCED IMMUNOASSAY AND TEST DEVICE

This work was partially funded by the National Institutes of Health, DHHS, under the Superfund Basic Research and Education Program, NIEHS ES-05950. Fabrication of electrodes was performed at the National Nanofabrication Facility which is supported, in part, by the National Science Foundation under Grant ECS-8619049.

FIELD OF THE INVENTION

The present invention relates to a method for detecting or quantifying one or more analytes, and a test device used in the method. More particularly, the invention relates to a single-use test strip for use in an immunomigration assay employing marker-loaded liposomes and electrochemical detection for signal amplification and quantitation.

BACKGROUND OF THE INVENTION

There is an increasing need for rapid, reliable, and inexpensive methods for detecting and measuring pollutants and contaminants in the environment and in food sources. Conventional analytical methods such as high pressure liquid chromatography, gas chromatography/mass spectroscopy, atomic absorption spectroscopy, etc. are particularly unsuitable for use in the field, because such methods are generally complex and employ instruments and equipment which are expensive and susceptible to damage from transport and possible contamination in the field. Gathering samples in the field for analysis at a remote laboratory is similarly unsatisfactory, because it may take a few days to several weeks from sample acquisition to obtain the results.

The need for simple, rapid, and inexpensive field assays has led to an investigation of immunoassays for surveying environmental contamination. Polychlorinated biphenyls (PCBs), for example, which were sold commercially in the United States under the Aroclor trademark, were industrial compounds used extensively as lubricants, fire retardants, immersion oils, dielectric and heat transfer fluids, as well as a multitude of other products. Safe, S. Toxicology 1990, 3, 51–88. They have contaminated an enormous variety of media, primarily as a result of careless use, disposal, and accidents, and have now been identified by the EPA as priority pollutants to be targeted for remediation under the national Superfund program. Extensive efforts have recently been undertaken to characterize Superfund sites by both the EPA and various environmental remediation firms. One of the chief obstacles to the prompt completion of such studies is the high cost and long turnaround time for conventional PCB analysis by off-site laboratories.

Immunoassays comprise one category of specific binding assays, which generally rely on the affinity of naturally occurring receptors or antibodies for specific compounds. The specific binding pairs employed in immunoassays are either an antigen or a hapten, and the antibody produced in an immune response to the antigen or hapten.

Competitive immunoassays are generally based upon the competition between a specific analyte, the amount of which is to be determined, and a labelled form of the analyte or an appropriate analog thereof, which is used as an indicator, for a limited number of available binding sites on a binding material specific for the analyte. Using a known amount of the labelled analyte, the amount of analyte in the sample can be determined by measuring the amount of the unbound labelled analyte, which in some systems is physically separated from the bound indicator during the assay. Alternatively, where it is possible to distinguish bound from unbound indicator, such as where detectable physical or chemical changes in the indicator occur as a result of the binding reaction, an assay can be completed without separating the bound and unbound indicator.

The types of materials commonly used as immunoassay label materials or markers include various enzymes, fluorescent dyes, chemiluminescent reactants, and radioisotopes. Such materials are often conjugated to the analyte, as in the case of enzymes and radioisotopes, or less frequently, carried within sacs such as animal erythrocytes, polymer microcapsules, or liposomes.

Immunoassays have been widely used for medical diagnosis for many years. More recently, immunoassays have been more broadly applied for the determination of toxic substances in the environment and in food. Practical applications for immunoassays in environmental analysis include evaluating the geographical scope and magnitude of pollutants, monitoring the fate and persistence of contaminants, and assessing the effectiveness of remediation efforts. Raw and processed foods must similarly be tested for chemical and biological contamination.

A wide variety of immunoassays, reagents, and test devices which exploit the interaction between the members of specific binding pairs to detect or measure a substance in a test sample have been developed. Sophisticated, automated immunoassay systems are successfully employed in laboratory settings, but there are also many types of portable sensing devices which can be used outside the laboratory. Some portable immunoassays and test devices have even been developed for use in the home by untrained individuals. Home pregnancy test kits are an example of such immunoassay test kits.

Immunoassay techniques have shown considerable promise for the characterization of PCB contamination. Most assays have chosen the ELISA (enzyme-linked immunosorbent assay) format which is often based on the competition between sample analyte and analyte-enzyme conjugates for a limited number of antibody binding sites. These methods offer many advantages such as speed, minimal sample cleanup, and high sensitivity and selectivity over standard laboratory techniques. Kaufman, B. M.; Clower, M. J. Assoc. Off. Anal. Chem. 1991, 74, 239–247. Van Vunakis, H. In *Immunochemical methods for environmental analysis*; Van Emon, J. M.; Mumma, R. O., Ed.; ACS: Washington, D.C., 1990; Vol. 442; 1–12. Furthermore, the analysis can, in many cases, be conducted in the field, thus reducing the delays and other logistical problems associated with transporting expensive samples to remote laboratories. Mapes, J. P.; McKenzie, K. D.; Stewart, T. N.; McClelland, L. R.; Studabaker, W. B.; Manning, W., B,; Friedman, S. B. Bull. Environ. Contam. Toxicol. 1993, 50, 219–225. However, ELISA tests still involve numerous solution changes, timed reactions, and a whole series of critical steps that can be a source of operator error when conducted in the field, under non-optimal conditions.

Several commercially available on-site ELISA tests have been developed to satisfy the demand for affordable and rapid site characterization for PCB contamination. Mapes, J. P.; McKenzie, K. D.; Stewart, T. N.; McClelland, L. R.; Studabaker, W. B.; Manning, W., B,; Friedman, S. B. Bull. Environ. Contam. Toxicol. 1993, 50, 219–225. Fribush, H. M.; Fisk, J. F. In *Environmental Lab;* 1992; 36–41. Engle, S. W.; Harrison, R. O.; Scallon, A.; Meckes, M. C. In *Superfund '92*; HMCRI-Hazardous Materials Control Research Institute, Washington, D.C., 1992. These kits are still estimated to cost between $25 and $50 per sample (obtained from the manufacturers' literature) and often require specially trained operators to obtain reproducible results, which introduces higher labor costs. Although this represents a great improvement over conventional analysis there still remains the impetus for the development of increasingly lower cost and easier to use on-site techniques. Hammock, B. D.; Gee, S. J.; Harrison, R. O.; Jung, F.; Goodrow, M. H.; Li, Q. X.; Lucas, A. D.; Szekacs, A.; Sundaram, K. M. S. In *Immunochemical methods for environmental analysis*; J. M. Van Emon and R. O. Mumma, Ed.; American Chemical Society; Washington, D.C., 1990; Vol. 442; 112–139.

An immunochromatographic assay method for whole blood samples is described in U.S. Pat. No. 4,594,327 to Zuk. At least one member of the specific binding pair is uniformly bound to the entire surface of a solid bibulous element. The element is contacted with the whole blood sample containing the analyte in an aqueous medium so that the sample traverses the element to define a border related to the amount of analyte. The analyte concentration is directly related to the distance the analyte has traversed. Zuk further describes determination of the border by a separate development step, such as an enzyme or chromophore signal production and amplification system.

U.S. Pat. No. 5,085,987 to Olson also describes an immunoassay employing a bibulous element such as a piece of paper affixed to plastic with adhesive. The element is contacted with the test solution suspected of containing the analyte, to which has been added an antibody for the analyte and a conjugate of the analyte and a label. The element contains a first receptor for the conjugate which is bound to a situs on the element separated from the contact portion, and a second receptor capable of binding the antibody for the analyte, which is bound to the element between the first receptor and the contact portion. The test solution moves along the element by capillary action. The situs is examined for the presence of conjugate, either by exposing the situs to a signal producing means capable of interacting with the label to produce a signal in a separate development step, such as an enzyme-catalyst-substrate system, or by directly measuring the signal from a radioactive label.

U.S. Pat. No. 4,939,098 to Suzuki, et al. discloses an immunoassay device for simultaneous determination of at least two components in a sample. At least two reagents, each of which reacts specifically with one of the components in the sample, are supported in optional places on a development layer. Residual components in the sample which do not react with the reagent first contacted by the sample continue to be moved past the place on the development layer where the first reagent is supported. After the movement of the unreacted components past each of the reagent places, the amount of the two reaction products still held in the development layer are measured. Test reagents may be included in liposomes, which are immobilized on the development layer by physical adsorption or chemical bonding.

In Suzuki, a detectable label substance such as a chelating agent, an enzyme or a fluorescent substance may be enclosed in the liposomes in addition to the antibody or antigen test reagents for qualitative or quantitative analysis of sample components. The liposomes or other label sacs are lysed by the antigen-antibody reaction or complement activity, to release label for detection or quantification. Suzuki further describes an electric measurement method in which the liposomes contain a substance detectable with electrodes. A solution of the liposomes is removed from the development layer, and the amount of the component to be measured is quantified from the amount of signal produced at the electrode.

As a result of the complexity of the device and method described in Suzuki, Suzuki's technique is not well-suited for use in the field, or for use by untrained personnel. High voltage is required for the electrophoretic separation method, for example.

Immunoassays employing liposomes for signal production are described in U.S. Pat. No. 4,874,710 to Piran and U.S. Pat. No. 4,703,017 to Campbell. In Piran, the sample containing the analyte is contacted with a binder for the analyte in the presence of a conjugate of a ligand coupled to a sac lysing agent. The ligand may be designed to bind either with the analyte or the binder. Unbound conjugate, which includes a sac lysing agent, comes into contact with immobilized liposomes, which release a detectable marker. Signal from the marker is measured in the aqueous assay medium. The binder and sacs may be placed on different portions of a solid support, such as a "dip stick" which may be inserted into and withdrawn from the assay medium.

Campbell discloses an immunoassay for determination of an analyte using a tracer, such as the analyte labelled with liposome-encapsulated markers. The tracer can be visually determined without instrumentation and without further treatment of the tracer (such as sac lysing). A binder for at least one of the analyte and the tracer is supported on a test area of a solid support, which is preferably nitrocellulose in the form of a card, test strip, or dipstick. Detection or quantification of the signal, e.g., color from a dye, is made in the test area of the device. Competitive, sandwich, and inhibition embodiments of the assay are disclosed.

The use of an agglutination-based portable assay, for on-site detection of drugs of abuse, has been reported. Parsons, R. G.; Kowal, R.; LeBlond, D.; Yue, V. T.; Neargarder, L.; Bond, L.; Garcia, D.; Slater, D.; Rogers, P. *Clin. Chem.* 1993, 39, 1899–1903. This system employs a modified hemagglutination inhibition mechanism, using blue-stained Duracytes, that is analyzed with paper chromatography. Duracytes are fixed human erythrocytes. In the method described in Parsons et al., the Duracytes are coated with anti-fluorescein antibody and combined with antisera to five drugs (amphetamines, cannabinoids, cocaine metabolites, opiates, and PCP). The test sample is added to this combination, and the entire mixture (test sample, Duracytes, and antisera) is loaded onto a multichambered vessel device. The device automatically distributes the mixture into distinct assay channels, each containing different dried flourescein-drug conjugates. Negative assays (no drug present) form an agglutinated reaction product (as a result of reactions between the Duracytes, the conjugate, and the anti-drug antibody), while positive assays show no agglutination. Agglutination results in the production of characteristic banded patterns in the channels showing a negative result.

Parsons et al. thus requires two different antibodies for agglutination, one coated on the Duracytes and one immobilized on a solid surface. In addition, Parsons relies on the production of signal for negative results, which is counterintuitive, and its narrow dynamic range for detection effectively limits its usefulness when quantitation is desired. Also, the range of markers which can be applied to the Duracytes is limited.

Immunoassays employing electrochemical detection are described in U.S. Pat. No. 4,822,566 to Newman, and Niwa, O.; Xu, Y.; Halsall, H. B.; and Heineman, W. R. Anal Chem. 1993, 65, 1559–1563 ("Niwa"). Newman describes a multilayer immunoassay device which relies on the movement of biological species into or out of a biological binding layer in the course of biospecific binding reactions. This movement changes the dielectric constant of the fluid medium containing the analyte, resulting in capacitance changes detected by a sensor. A capacitor comprised of an array of interdigitated copper and gold fingers (2 mil wide, 0.5 mil high, separated by 3 mil spaces) formed by photolithographic etching techniques is disclosed. Niwa describes an electrochemical enzyme immunoassay which employs an interdigitated array microelectrode cell to detect 4-aminophenol (PAP), produced during enzyme immunoassay of mouse IgG. The gold interdigitated array consisted of 50 pair of 3 or 5 $\mu$m wide microbands, spaced 2 $\mu$m apart. Silver-plated and unplated gold square electrodes were used as reference and auxiliary electrodes, respectively. The assay was conducted in microwells.

The devices and techniques in Newman and Niwa, however, are relatively complex. For example, the enzyme immunoassay described in Niwa is carried out through multiple steps to completion on an immunowell device, and the reaction solution is then transferred to a separate electrochemical detection device.

In view of the above-noted deficiencies and complexities of prior techniques for use as rapid, reliable, and simple field assays, the need remains for technology which will accurately detect and determine analytes such as environmental and food contaminants.

SUMMARY OF THE INVENTION

The present invention provides a method and device for detecting or quantifying an analyte in a test sample employing an automatic electrochemical signal production and amplification method. The test device includes an absorbent material, having a contact portion proximate to one end for contact with and uptake of the test solution. Positioned away from the first end of the absorbent material, there is an electrochemical measurement portion having a first conductor and a second conductor. Each conductor comprises a plurality of fingers disposed on the absorbent material, and the fingers of the first conductor are interdigitated with the fingers of the second conductor. The first and second conductors can be adapted for electrical connection with one another through an appropriate electrochemical analyzer. A liposome lysing agent is also bound to the absorbent material, either in a liposome lysing portion positioned between the contact portion and the electrochemical measurement portion, or the liposome lysing agent is bound to the absorbent material in an area which partially or completely overlaps the electrochemical measurement portion.

In another embodiment of the invention, the test device further includes a competitive binding portion positioned between and segregated from the contact and liposome lysing portions. A binding material for the analyte is bound to the competitive binding portion.

In yet another embodiment, the test device further includes a capture portion positioned between and segregated from the contact and liposome lysing portions. A capture probe selected to at least partially hybridize with a target nucleic acid sequence is bound to the capture portion.

The present invention further provides a method for detecting or quantifying an analyte in a test sample utilizing a test device which relies on electrochemical detection of an electroactive marker. A binding material specific for the analyte is combined with a conjugate of an analyte analog and liposomes comprising an electroactive marker and the test sample in an electrolyte solution. The resulting mixture is incubated for a time sufficient to allow competition between any analyte present in the test sample and the conjugate, and then the mixture is contacted with a contact portion proximate to one end of the absorbent material of the test device. The mixture is allowed to traverse the absorbent material, via capillary action, from the contact portion, through an electrochemical-measurement portion of the absorbent material which is positioned away from the end to which the contact portion is proximate. The electrochemical measurement portion includes first conductor and a second conductor. Each conductor comprises a plurality of fingers disposed on the absorbent material, and the fingers of the first conductor are interdigitated with the fingers of the second conductor. The first and second conductors can be adapted for electrical connection with one another through an appropriate electrochemical analyzer. A liposome lysing agent is also bound to the absorbent material, either in a liposome lysing portion positioned between the contact portion and the electrochemical measurement portion, or the liposome lysing agent is bound to the absorbent material in an area which partially or completely overlaps the electrochemical measurement portion. The liposome lysing portion is segregated from the contact portion. As the test solution traverses the absorbent material of the test device as described above, the flow of electrolyte test solution through the electrochemical measurement portion completes a circuit between the first and second conductors, causing current to flow. Also, the liposomes come into contact with the liposome lysing agent, and lysis of the liposomes causes release of the electroactive marker. The current flowing between the first and second conductors is then correlated with the presence or amount of the analyte in the sample.

In another embodiment, the invention provides a method for detecting or quantifying an analyte, employing a test device modified to include a competitive binding zone. Specifically, the test device includes an absorbent material, having a contact portion at or proximate to a first end of the absorbent material, an electrochemical measurement portion positioned on the absorbent material away from the first end, a liposome lysing portion segregated from the contact portion and having a liposome lysing agent bound to the liposome lysing portion, and a competitive binding portion positioned between and segregated from the contact portion and the liposome lysing portion. The competitive binding portion has a binding material for the analyte bound thereto. The liposome lysing portion is either positioned between the contact and electrochemical measurement portions, or it partially or completely overlaps the electrochemical measurement portion. The test device further includes a competitive binding portion, which has a binding material for the analyte bound to it, positioned between and segregated from the contact and liposome lysing portions on the absorbent material.

In this method, an electrolyte solution of the analyte and a conjugate of an analyte analog and liposomes is prepared. The liposomes comprise an electroactive marker. The solution is contacted with the contact portion of the absorbent material, and allowed to migrate from the contact portion through the electrochemical measurement portion of the absorbent material. As the solution migrates into and across the liposome lysing portion, the liposomes are lysed by the liposome lysing agent to release the marker, and an electrical connection between the first and second conductors is established causing current to flow between the first and second conductors. The presence or amount of the current is detected and correlated to the presence or amount of the analyte in the test sample.

In another embodiment, a method for detecting or quantifying a target nucleic acid sequence is provided. The test device employed in this embodiment is like that described above for the competition format, but the competitive binding portion described above is replaced with a capture portion. The capture portion has a capture probe bound thereto. The capture probe is a nucleic acid sequence selected to at least partially hybridize with a portion of the target nucleic acid sequence under investigation. The assay is conducted as described above for the competition format, but the analyte analog-liposome conjugate is replaced in this embodiment by a conjugate prepared by attaching reporter nucleic acid sequences to liposomes which encapsulate the electroactive marker. The reporter nucleic acid sequence is selected to at least partially hybridize with a portion of the target nucleic acid sequence other than the portion of the target sequence for which the capture probe is selected.

The conjugate is combined and incubated with the test sample in an electrolyte solution to prepare the test mixture. As the test mixture traverses the absorbent material, the target sequence, which, if present, has at least partially hybridized to the reporter sequence, now at least partially hybridizes to the capture sequence bound to the absorbent material, forming a "sandwich." Unbound conjugate, comprising the marker-encapsulating liposomes, is free to continue to traverse the absorbent material through the liposome lysing portion, where the liposomes are lysed to release the electroactive marker, which moves along the absorbent material as described above and completes the circuit between the electrodes. In this embodiment, however, the amount of current produced in the electrochemical measurement portion is inversely proportional to the amount of target nucleic acid sequence present in the sample.

The device and method of the invention can be used directly in the field. The device is used only once, and, therefore, is free from residual environmental contaminants other than what may be present in the sample to be measured. Samples can be assayed within minutes after collection, with the results immediately available on-site. In addition, the device and method of the invention are less complex than many of the prior materials and methods. The ability to deliver quantitative results without additional steps for spectrophotometric or fluorimetric analysis, is an advantage of the present electrochemical device and method over devices and methods which employ dyes and fluorescent materials as markers.

In addition, electroactive marker-loaded liposomes as used in the device and method of the invention provide a highly sensitive, rapid or even instantaneous signal production/amplification system. Furthermore, in the competition and aggregation formats described above, the amount of marker measured in the electrochemical measurement portion of the absorbent material of the test device is directly proportional to the analyte concentration in the sample. This feature of the invention provides a particular advantage over prior test devices and immunoassays, providing an intuitive correlation between signal strength and analyte concentration. Electrochemical detection offers greater sensitivity than calorimetric determination and is comparable to fluorimetry or chemiluminescence. In addition, the present invention provides quantitative results which can be obtained directly from the electroanalyzer or other detection instrumentation to which the test device is connected, without the need to transfer the device to a separate optical measurement device. Also, electrochemical detection allows for testing in solutions or mixtures which are highly colored or include particulate matter, and which, therefore, would interfere with optical detection.

Interdigitated electrode arrays are particularly suitable for test strip analysis due to their planar configuration and their inherent sensitivity for electrochemical measurements. Microelectrodes fabricated in an interdigitated array have inherent advantages in signal detection over more conventional electrode configurations. These advantages can only be realized with electrodes of very small dimensions due to the theoretical relationships between electrode geometry and ionic diffusion. Scaling down the size of an individual electrode has the advantage of increasing the rate of mass transport, increasing the signal-to-noise (faradaic/charging current) ratio, and decreasing ohmic signal losses, as described in M. Fleischmann, S. Pons, D. R. Rolison, P. P. Schmidt, Eds. *Ultramicroelectrodes* (Datatech Systems, Inc., Morganton, N.C. 1987), which is hereby incorporated by reference. Advantages of microelectrodes are also described in J. O. Howell, Voltammetric Microelectrodes, Bioanalytical Systems, Inc., West Lafayette Ind. 47906, hereby incorporated by reference.

Advantages of fabricating small electrodes in interdigitated arrays go even further by allowing redox cycling of ions back and forth between anode(s) and cathode(s). See O. Niwa, Y. Xu, B. H. Halsall, W. R. Heineman, Anal. Chem. 65, 1559–1563 (1993) and O. Niwa, H. Tabei, Anal. Chem. 66, 285–289 (1994), each of which is hereby incorporated by reference. This generates much larger currents for detection and allows for the use of extremely small sample volumes. By using a dual potentiostat and a four-electrode system with an interdigitated array, it is possible to almost completely eliminate charging current. This results in a greater signal-to-noise ratio and allows for the use of extremely high scan rates. See O. Niwa, M. Morita, H. Tabei, Anal. Chem. 62, 447–452 (1990) and C. Chidsay, B. J. Feldman, C. Lundgren, R. W. Murray, Anal. Chem. 58, 601–607 (1986), which are hereby incorporated by reference. Furthermore, the sophisticated electronics needed to detect the very small currents associated with individual microelectrode filaments are not necessary due to the summation of current from the large array of microelectrodes.

BRIEF DESCRIPTION OF THE DRAWINGS

FIG. 5 is a schematic depiction of competitive binding events which occur on the test device employed in the competition embodiment (FIG. 5A) and during the incubating step in accordance with the aggregation embodiment (FIG. 5B) of the present invention.

DETAILED DESCRIPTION OF THE INVENTION

Figure 1:
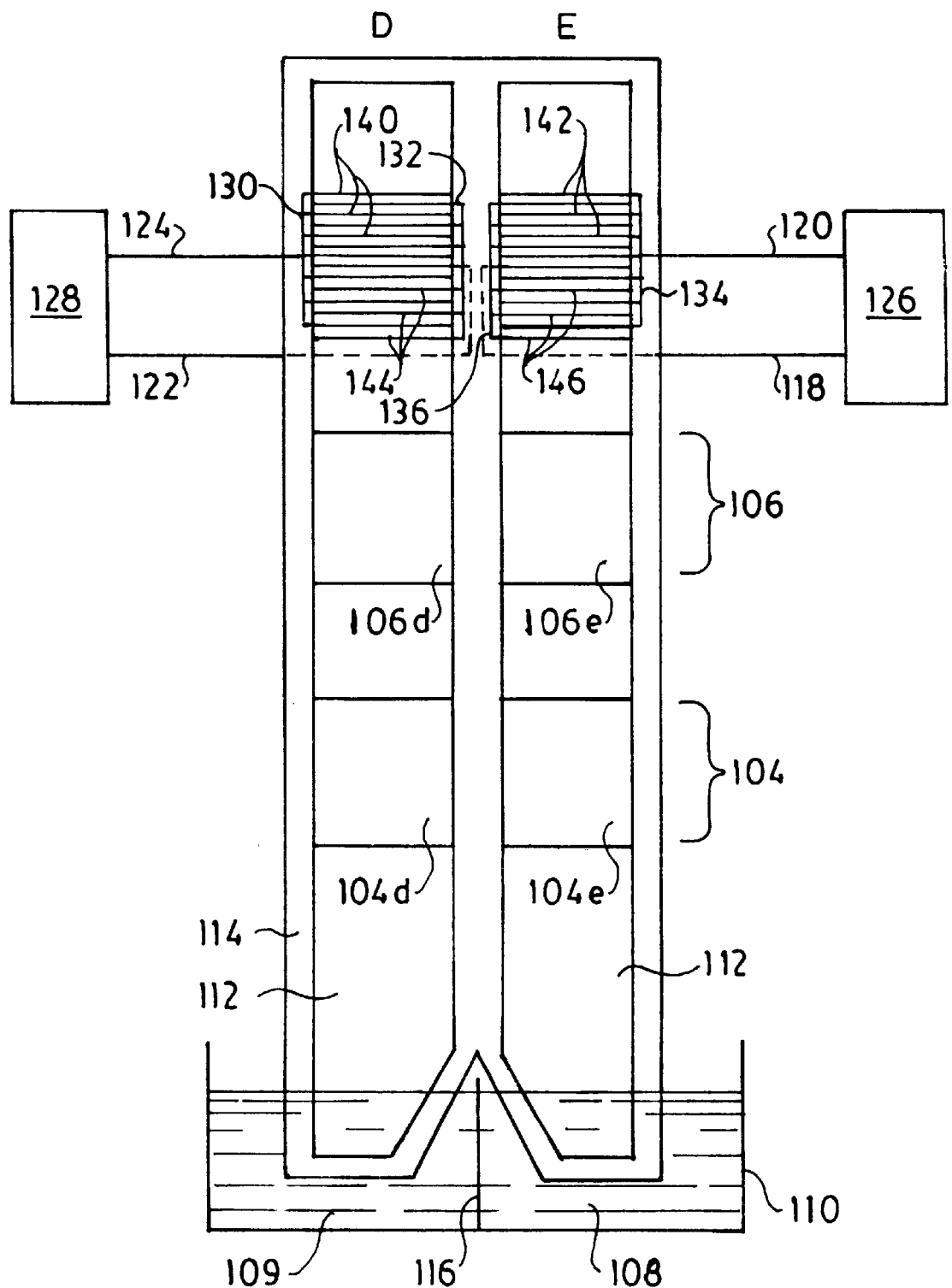
FIG. 1 is a schematic of a multiple channel test device in accordance with the competition embodiment of the invention.

As described above, the present invention provides a method and device for detecting or quantifying an analyte in a test sample employing an automatic electrochemical signal production and amplification method.

In one embodiment, referred to herein as the "aggregation" embodiment or format, the test device includes an absorbent material which has a contact portion proximate to one end for contact with and uptake of a test mixture. An electrochemical measurement portion having a first conductor and a second conductor is positioned away from the first end of the absorbent material. Each conductor (or electrode) comprises a plurality of fingers disposed on the absorbent material, and interdigitated with the fingers of the other conductor. The first and second conductors can be adapted for electrical connection with one another through an appropriate electrochemical analyzer. A liposome lysing agent is also bound to the absorbent material, either in a liposome lysing portion positioned between the contact portion and the electrochemical measurement portion, or the liposome lysing agent is bound to the absorbent material in an area which partially or completely overlaps the electrochemical measurement portion.

In another embodiment of the invention, referred to herein as the "competition" or "competitive binding" embodiment or format, the test device is as described above for the aggregation format, but also includes a competitive binding portion positioned between and segregated from the contact and liposome lysing portions. A binding material for the analyte is bound to the competitive binding portion.

In yet another embodiment, the test device further includes a capture portion positioned between and segregated from the contact and liposome lysing portions. A capture probe selected to at least partially hybridize with a target nucleic acid sequence is bound to the capture portion.

The present invention further provides a method for detecting or quantifying an analyte in a test sample utilizing a test device which relies on electrochemical detection of an electroactive marker. In the aggregation format, a binding material specific for the analyte is combined with a conjugate of an analyte analog and liposomes comprising an electroactive marker and the test sample in an electrolyte solution. The resulting mixture is incubated for a time sufficient to allow competition between any analyte present in the test sample and the conjugate, and then the mixture is contacted with a contact portion proximate to one end of the absorbent material of the test device. During incubation, a competition takes place between the analyte, and the analyte-analog tagged liposomes, for the analyte-specific antibody. The lower the concentration of analyte in the sample, the greater the number of multi-liposome aggregates that form in the test mixture, as discussed more fully below. As the mixture is allowed to traverse the absorbent material, via capillary action, from the contact portion, through an electrochemical measurement portion of the absorbent material which is positioned away from the end to which the contact portion is proximate, the aggregate do not migrate, but are trapped in the matrix of the absorbent material at or near the contact portion. Disaggregated liposomes, formed in conjunction with the analyte, are free to migrate along the absorbent material.

The electrochemical measurement portion of the device used in the aggregation format includes first conductor and a second conductor. Each conductor comprises a plurality of fingers disposed on the absorbent material, and the fingers of the first conductor are interdigitated with the fingers of the second conductor. The first and second conductors can be adapted for electrical connection with one another through an appropriate electrochemical analyzer. A liposome lysing agent is also bound to the absorbent material, either in a liposome lysing portion positioned between the contact portion and the electrochemical measurement portion, or the liposome lysing agent is bound to the absorbent material in an area which partially or completely overlaps the electrochemical measurement portion. The liposome lysing portion is segregated from the contact portion. As the test solution traverses the absorbent material of the test device as described above, the flow of electrolyte test solution through the electrochemical measurement portion completes a circuit between the first and second conductors, causing current to flow. Also, the liposomes come into contact with the liposome lysing agent, and lysis of the liposomes causes release of the electroactive marker. The magnitude of the current flowing between the first and second conductors is then correlated with the presence or amount of the analyte in the sample.

In the competition embodiment, the invention provides a method for detecting or quantifying an analyte, employing a test device modified to include a competitive binding zone. Specifically, the test device includes an absorbent material, having a contact portion at or proximate to a first end of the absorbent material, an electrochemical measurement portion positioned on the absorbent material away from the first end, and a liposome lysing portion segregated from the contact portion and having a liposome lysing agent bound to the liposome lysing portion. The liposome lysing portion is either positioned between the contact and electrochemical measurement portions, or it partially or completely overlaps the electrochemical measurement portion. The test device further includes a competitive binding portion, which has a binding material for the analyte bound to it, positioned between and segregated from the contact and liposome lysing portions on the absorbent material.

In this method, an electrolyte solution of the analyte and a conjugate of an analyte analog and liposomes is prepared. The liposomes comprise an electroactive marker. The solution is contacted with the contact portion of the absorbent material, and allowed to migrate from the contact portion through the electrochemical measurement portion of the absorbent material. As the solution migrates into and across the liposome lysing portion, the liposomes are lysed by the liposome lysing agent to release the marker, and an electrical connection between the first and second conductors is established causing current to flow between the first and second conductors. The presence or amount of the current is detected and correlated to the presence or amount of the analyte in the test sample.

In another embodiment, a method for detecting or quantifying a target nucleic acid sequence is provided. The test device employed in this embodiment is like that described above for the competitive format, but the competitive binding portion described above is replaced with a capture portion. The capture portion has a capture probe bound thereto. The capture probe is a nucleic acid sequence selected to at least partially hybridize with a portion of the target nucleic acid sequence under investigation. The assay is conducted as described above, but the analyte analog-liposome conjugate is replaced in this embodiment by a conjugate prepared by attaching reporter nucleic acid sequences to liposome which encapsulate the electroactive marker. The reporter nucleic acid sequence is selected to at least partially hybridize with a portion of the target nucleic acid sequence other than the portion of the target sequence for which the capture probe is selected.

The conjugate is combined and incubated with the test sample to prepare the test mixture, which is then contacted with the contact portion of the absorbent material. As the test mixture traverses the absorbent material, the target sequence, which, if present, has at least partially hybridized to the reporter sequence, now at least partially hybridizes to the capture sequence bound to the absorbent material, forming a "sandwich." Unbound conjugate, comprising the marker-encapsulating liposomes, is free to continue to traverse the absorbent material through the liposome lysing portion, where the liposomes are lysed to release the electroactive marker, which moves along the absorbent material as described above and completes the circuit between the electrodes. In this embodiment, however, the amount of current produced in the electrochemical measurement portion is inversely proportional to the amount of target nucleic acid sequence present in the sample. Preparation of the conjugate, attachment of the capture probe to the absorbent material, and other aspects of this embodiment are described in co-pending provisional application Ser. No. 60/015,373, which is hereby incorporated by reference. It should be noted that the capture portion in this embodiment replaces the competitive binding portion in the competition embodiment, and, therefore, references herein concerning the location and placement of the latter on the absorbent material should be construed to refer also to the capture portion.

By "analyte" is meant the compound or composition to be measured that is capable of binding specifically to an binding material.

By "binding material" is meant a bioreceptor molecule such as an immunoglobulin or derivative or fragment thereof having an area on the surface or in a cavity which specifically binds to and is thereby defined as complementary with a particular spatial and polar organization of another molecule—in this case, the analyte. The binding material, such as an antibody, can be monoclonal or polyclonal and can be prepared by techniques that are well known in the art such as immunization of a host and collection of sera or hybrid cell line technology. The binding material may also be any naturally occurring or synthetic compound that specifically binds the analyte of interest.

IgG is a preferred binding material in accordance with the invention as it is bivalent and, therefore, tends to enhance the formation of aggregates of the conjugate and the binding material. IgM may be particularly preferred for certain applications, particularly in the aggregation embodiment of the present invention, as its 10 binding sites per molecule would be expected to promote the formation of large aggregates.

As is discussed in greater detail below, the method of the invention employs a conjugate of marker-encapsulating liposomes and an analyte analog. Certain analytes of interest may be so intractable as to make direct conjugation with the liposome inconvenient, difficult, or even impossible. In such cases, it will be necessary to employ a reactive analog of the analyte of interest to prepare the conjugate. Thus, by "analyte analog" is meant either the analyte or an analog of the analyte which will react with or bind to the liposomes. When an analog is employed, however, it is necessary that the particular characteristics of the analyte necessary for recognition by the binding material in the competition reaction be present in the analyte analog conjugated with the liposomes.

The electrolytic mixture formed by combining the binding material, the conjugate, and the test sample, in the aggregation embodiment, or the conjugate and the test sample, in the competition embodiment, or the reporter sequence-liposome conjugate and the test sample suspected to contain the target nucleic acid sequence, may be a solution, suspension, dispersion, or other mixture.

By "absorbent material" is meant a porous material having a pore size of from 0.05 $\mu$m to 50 $\mu$m, preferably from 0.45 $\mu$m to 5 $\mu$m, which is susceptible to traversal by an aqueous medium in response to capillary force. Such materials may be natural polymeric materials, particularly cellulosic materials, such as fiber-containing papers, e.g., filter paper, chromatographic paper, etc.; synthetic or modified naturally occurring polymers, such as nitrocellulose, cellulose acetate, poly(vinyl chloride), polyacrylamide, cross linked dextran, agarose, polyacrylate, activated nylon, etc.; either used by themselves or in conjunction with a support, as described below. Nitrocellulose is a preferred absorbent material.

The absorbent material may be polyfunctional or be capable of being polyfunctionalized to permit covalent bonding of receptors as well as to permit bonding of other compounds which form a part of the signal producing system.

The absorbent material which is employed in the test device and method of the invention is generally a cellulose ester with nitrocellulose giving exceptionally good results. It is to be understood that the term "nitrocellulose" refers to nitric acid esters of cellulose, which may be nitrocellulose alone, or a mixed ester of nitric acid and other acids, and in particular, aliphatic carboxylic acids having from one to seven carbon atoms, with acetic acid being preferred. Such materials, which are formed from cellulose esterified with nitric acid alone, or a mixture of nitric acid and another acid such as acetic acid, are often referred to as nitrocellulose paper.

Although nitrocellulose is a preferred material for producing the test device, it is to be understood that other materials, having a surface area sufficient for supporting the binding material, liposome lysing agent, and any other agents to be immobilized thereon in a concentration as hereinbelow described, and a pore size suitable for accumulating aggregates formed from the conjugate and the binding material, for the aggregation embodiment, may also be employed for producing such test devices.

In general, the absorbent material which is used in the device and method of the invention has a surface area such that is capable of supporting the liposome lysing agent, in both the aggregation and competition embodiments, in an excess amount, i.e. in an amount sufficient to effectively lyse the liposomes and release the electroactive marker as the test mixture migrates across the liposome lysing portion.

Absorbent materials having high surface areas (such as nitrocellulose) are particularly preferred for some applications in that the binding material may be supported on such materials in a high concentration. It is to be understood, however, that the concentration of binding material which is actually used is dependent in part on the binding affinity of the binding material. Accordingly, the scope of the invention is not limited to a particular concentration of binding material on the absorbent material.

Application of binding materials and liposome lysing agents to the absorbent material may be accomplished by well-known techniques, for example, by spraying or spotting a solution of those materials onto the absorbent material.

The binding material can be bound to the absorbent material by adsorption, rather than covalent bonding, as long as such binding is non-diffusive. This will involve contacting the absorbent material with a solution containing the materials to be bound to the material and allowing the material to dry. In general, this procedure will be useful only where the absorbent material is relatively hydrophobic or has a high surface charge, and subsequent treatment with proteins, detergents, polysaccharides, or other materials capable of blocking nonspecific binding sites will be required.

Before or after application of the binding material and liposome lysing agent to the appropriate portion on the absorbent material, the residual nonspecific binding capacity of the absorbent material can be, and preferably is, saturated or blocked with one or more types of proteins or other compounds such as polyvinylpyrrolidone, polyvinylalcohol, other suitable polymeric blocking agents etc., which do not specifically bind the materials to be employed in the assay. Blocking is generally carried out after the binding material and liposome lysing agent is applied to the strip, but it may be possible to block the strip before the binding material is applied depending on the method of application, the particular blocking agent and absorbent material employed. Similarly, the order of the steps of blocking the absorbent material and applying the liposome lysing agent may vary depending on the particular assay conditions and components employed. Thus, for example, the residual binding capacity of the substrate may be blocked so as to prevent nonspecific binding by the use of bovine serum albumin, as described in Towbin, et al., *Proc. Nat'l. Acad. Sci.,* 76 (1979) 4350, which is hereby incorporated by reference. The techniques for preventing non-specific binding are generally known in the art, and such techniques are also generally applicable to preventing nonspecific binding in the assay of the present invention. Examples of particularly suitable techniques for blocking with polyvinylpyrrolidone and polyvinylalcohol are described, for example, Bartles, et al. *Anal. Biochem.,* 140 (1984) 784, and in British Patent Specification GB 2204398 A, respectively, which are hereby incorporated by reference.

In conjunction with a blocking agent or agents, a surfactant may be applied to the absorbent material in a concentration sufficient to promote homogeneous flow of the test solution across the test device, to facilitate migration of the analyte analog-liposome conjugate without lysis of the liposomes. Suitable surfactants include Brij™ (polyoxyethylene ether), Tween 20™ (polyoxyethylenesorbitan monolaurate), Triton X-100™ (t-octylphenoxypolyethoxyethanol), sodium dodecylsulfate, n-octyl-β-D-glucopyranoside, Span 20™, Nonindet P-40, Chapso™, Turgitol™ and sodium dioxycholate. The concentration of the surfactant(s) employed in a blocking solution will depend, in part, upon the liposome composition. In general, surfactants may be incorporated in a concentration of from about 0 to about 0.01 volume percent of the blocking solution, preferably from about 0.001 to about 0.005 volume percent of the blocking solution. It is important that the concentration of surfactant applied to the absorbent material be controlled, as premature lysis of the liposomes may occur if the surfactant concentration is too high. Tween 20™ is a preferred surfactant for use in a blocking solution.

Without being bound by theory, it appears that polyvinylpyrrolidone assists in the accumulation of aggregates on the absorbent material, particularly for "Liposome-Antibody Aggregation"-type aggregates shown in FIG. 5B, described more fully below.

The blocking agents block nonspecific binding sites on the absorbent material. The blocking agents are selected from the group consisting of proteinaceous blocking reagents capable of inhibiting binding of molecules having a molecular weight of greater than about 1000 with said absorbent material and polymer blocking reagents capable of inhibiting binding of molecules having a molecular weight of less than about 1000 with said absorbent material. The proteinaceous blocking reagent may be selected from the group consisting of gelatin, non-fat dry milk, bovine serum albumin, and keyhold limpet hemocyanin. The polymer blocking reagent may be selected from the group consisting of polyvinylpyrrolidone and polyvinylalcohol, and the surfactant may be selected from the group consisting of polyoxyethylene ethers, polyoxyethylenesorbitan monolaurate, t-octylphenoxypolyethoxyethanol, and sodium dodecylsulfate, octylglucopyranoside, and sodium dioxycholate.

Figure 3:
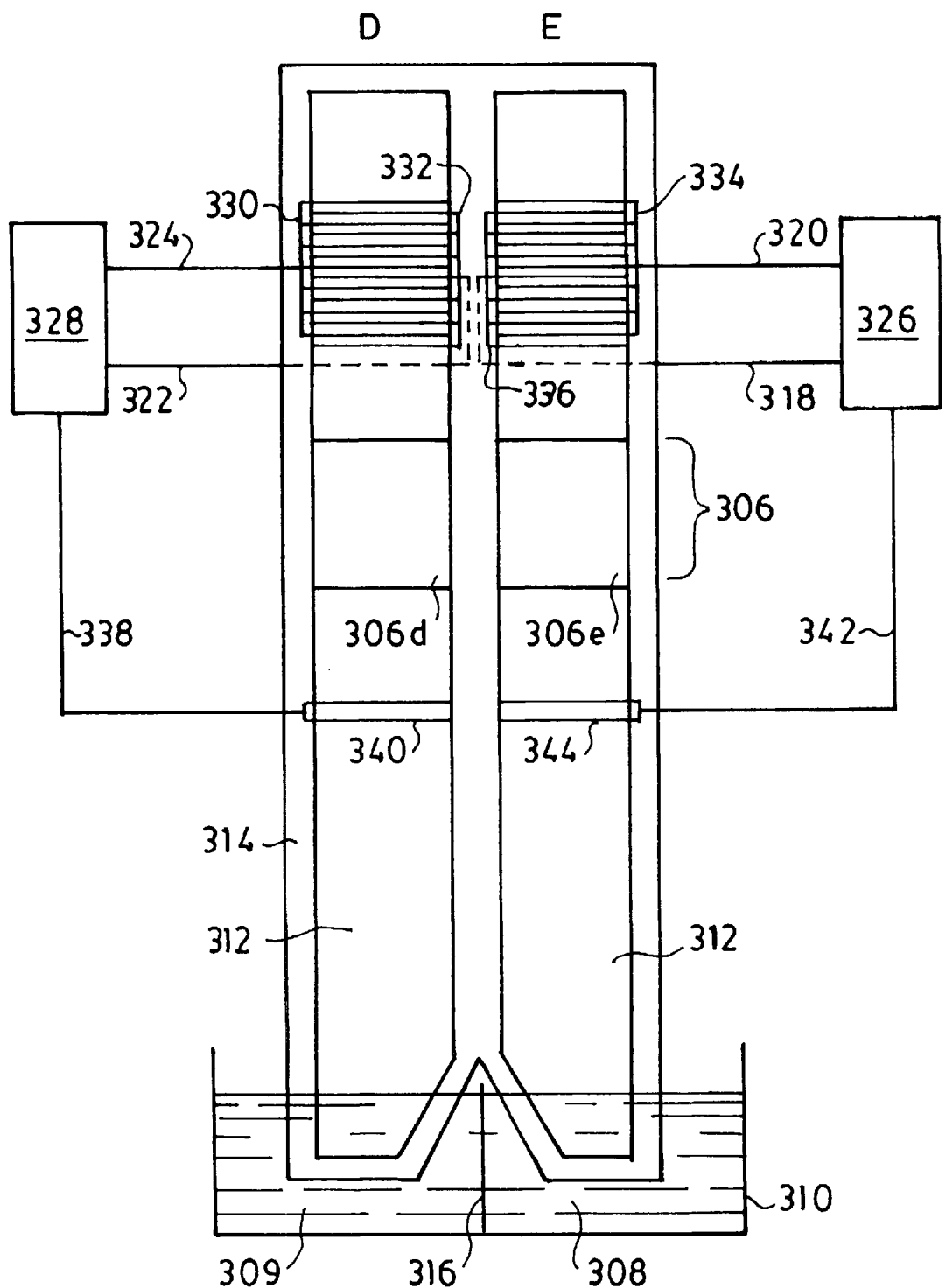
FIG. 3 is a schematic of a multiple channel test device in accordance with the aggregation embodiment of the invention.

The absorbent material can be a single structure such as a sheet cut into strips. The absorbent material can be mounted on a support material, described more fully below. On the other hand, the absorbent material may provide its own support. In one embodiment of the invention, the test device is a strip of particulate material bound to a support or solid surface such as found, for example, in thin-layer chromatography. The absorbent material can be a sheet having lanes thereon, or be a uniform sheet capable of division into separate lanes by physical removal of the absorbent material from the support to induce lane formation, wherein a separate assay can be performed in each lane as shown in FIGS. 1 and 3. The absorbent material can have a shape that is rectangular, circular, oval, trigonal, or the like, provided that there is at least one direction of traversal of a test mixture by capillary migration. Other directions of traversal may occur such as in an oval or circular piece contacted in the center with the test mixture. However, the main consideration is that there be one direction of flow from the contact portion through the measurement portion. In this discussion strips of absorbent material are described by way of illustration and not limitation.

The absorbent material of the test devices in accordance with the aggregation embodiment of the present invention preferably comprises a region for accumulation of aggregates formed from the conjugate and the binding material, as described in more detail, below. This region for accumulation is positioned away from the liposome lysing agent, and either between the liposome lysing agent and the contact portion, or in the contact portion.

In constructing the test devices in accordance with the invention, it is desirable to position the electrochemical measurement portion as close as possible to the contact portion (for the aggregation embodiment) and the competitive binding portion (for the competition embodiment) in order to minimize the time necessary for the test mixture to reach and pass through the measurement portion. However, it is important that the electrochemical measurement portion and contact portion (or competitive binding portions) not be so close as to contact one another, and to avoid having the test mixture come in contact with the electrochemical measurement portion other than by capillary transport of the test mixture through the measurement portion. In other words, the electrochemical measurement and contact portions should be separated sufficiently to avoid premature or unwanted contamination of the measurement portion through human error in manipulating the device. When there are multiple measurement portions positioned on the absorbent material (as described below for multi-analyte testing) the individual measurement zones may be close to one another and may, in certain cases, even overlap.

FIG. 1 is a schematic of a test device in accordance with the competition embodiment of the invention, depicted immediately after insertion into control solution 109 and test mixture or solution 108, which are held in tray 110 having partition 116 extending across the entire width of tray 110 to divide tray 110 into separate compartments for the control solution and test mixture. As shown in FIG. 1, absorbent material 112 is mounted on support 114. The test device shown in FIG. 1 is divided into two channels, namely, control channel D and test channel E, and competitive binding portions 104 and measurement portions 106. Control channel D includes competitive binding portion 104d, which has a binding material for the analyte of interest non-diffusively bound thereto. Control channel D further includes liposome lysing portion 106d, which has a liposome lysing agent non-diffusively bound thereto. Test channel E similarly has competitive binding portion 104e, which has been constructed to recognize and bind the analyte, and liposome lysing portion 106e, which includes a liposome lysing agent, as described above.

The test device shown in FIG. 1 further includes an electrochemical measurement portion, wherein absorbent material 112 is in contact with first conductors 130 and 134 in channels D and E, respectively, and second conductors 132 and 136, in channels D and E, respectively. First conductors 130 and 134 have fingers 140 and 142, respectively, which are interdigitated with fingers 144 and 146 of second conductors 132 and 136, respectively. In channel D, first conductor 130 and second conductor 132 are adapted for electrical connection with one another through leads 124 and 122, respectively, via potentiostat or electroanalyzer 128, Similarly, in channel E, first conductor 134 and second conductor 136 are adapted for electrical connection with one another through leads 120 and 118, respectively, via potentiostat 126.

According to the embodiment of the invention shown in FIG. 1, the contact portion of each channel of the test strip is the end of the strip to be inserted into the test or control solutions.

Test mixture 108 is typically prepared, as described below, by combining a sample known or suspected to contain the analyte with the analyte analog-liposome conjugate in an aqueous, electrolytic medium. In accordance with the embodiment shown in FIG. 1, control solution 109 is similarly prepared to have the same concentration of the conjugate as test mixture 108, and a known concentration of analyte in an electrolytic mixture.

In use, the contact portion of absorbent material 112 of control channel D is inserted into control solution 109, while the contact portion of absorbent material 112 of test channel E is inserted into test mixture 108. Wetting of absorbent material 112 by capillary action is allowed to continue at least until the electrochemical measurement portions defined by, and in contact with, conductors 130, 132, 134, and 136 are wet with control solution 109 and test mixture 108, respectively. As control solution 109 and test mixture 108 traverse channels D and E through competitive binding portions 104d and 104e, the analyte in control solution 109 and test mixture 108 competes with the analyte analog-liposome conjugate in mixtures for available binding sites on the specific binding material bound to competitive binding portions 104d and 104e. Control mixture 109 and test mixture 108 continue to traverse channels D and E of the test device into and through liposome lysing portions 106d and 106e, where the liposomes in the conjugate are lysed by the liposome lysing agent, releasing the electroactive marker they contain. The released marker is then carried by the migrating mixtures, via capillary action, into and through the electrochemical measurement portion of each channel. As the electrolytic mixtures pass through the absorbent material, an electrical circuit is completed between the fingers of the first and second conductors in contact with the absorbent material in each channel. The current flowing between the conductors is then detected and/or measured and correlated with the presence or amount of the analyte.

The test device shown schematically in FIG. 1 can be modified to include an additional channel or channels to provide linear interpolation and verification of response. For example, a three-channel device can be constructed for the simultaneous measurement of the analyte in a test sample and high- and low-level control compositions. It should also be recognized that single channel devices are within the scope of the present invention.

Figure 2A:
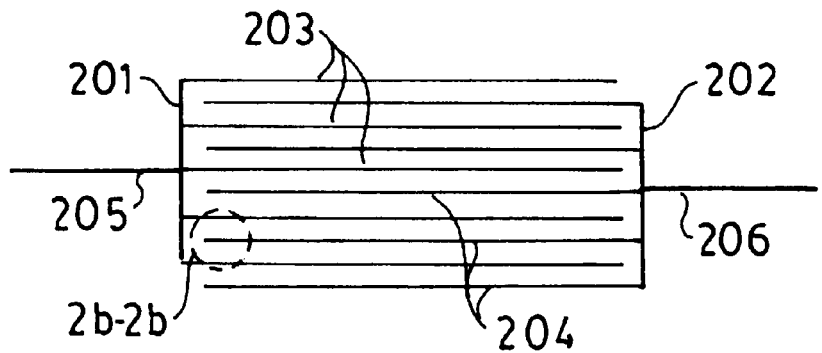
FIG. 2*a* is an enlarged view of an interdigitated electrode array as shown in FIG. 1.
Figure 2B:
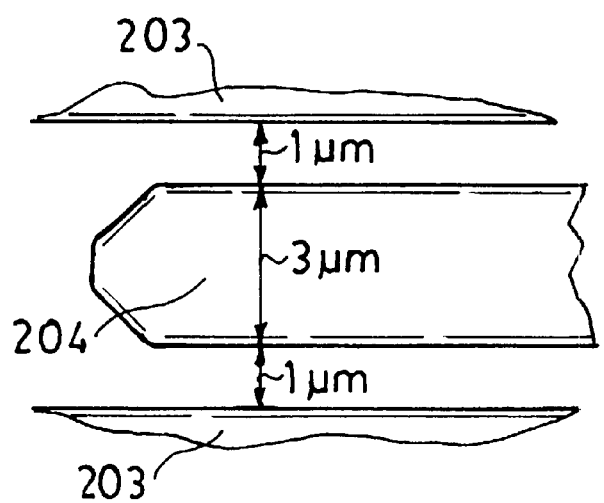
FIG. 2*b* is an exploded view of a portion of the electrode array shown in FIG. 2*a*.

FIG. 2 shows an enlarged view of the interdigitated electrode arrays shown in the electrochemical measurement portions in FIGS. 1 and 3. First conductor 201 has fingers 203, which are interdigitated with fingers 204 of second conductor 202. First conductor 201 can be connected via lead 205 with second conductor 202 via lead 206 through appropriate instrumentation.

FIG. 3 is a schematic of a test device in accordance with the aggregation embodiment of the invention, depicted immediately after insertion into control mixture 309 and test mixture 308, which are held in tray 310 having partition 316 extending across the entire width of tray 310 to divide tray 310 into separate compartments for the control and test mixtures. As shown in FIG. 3, absorbent material 312 is mounted on support 314. The test device shown in FIG. 3 is divided into two channels, namely, control channel D and test channel E, with liposome lysing portions 306. Control channel D includes liposome lysing portion 306d, which, as described above, has a liposome lysing agent bound thereto. Test channel E similarly has liposome lysing portion 306e, which also has a liposome lysing agent bound thereto.

The test device shown in FIG. 3 further includes an electrochemical measurement portion, defined by and in contact with first conductor 330 and second conductor 332 in channel D, and first conductor 334 and second conductor 336 in channel E. The fingers of first and second conductors 330 and 332, and of first and second conductors 334 and 336, are interdigitated to form an electrode array. Absorbent material 312 is further in contact with reference electrodes 340 and 344 in channels D and E, respectively. First conductor 330, second conductor 332, and reference electrode 340 are each connected to one another through potentiostat or electroanalyzer 328 via leads 324, 322, and 338 respectively. Similarly, first conductor 334, second conductor 336, and reference electrode 344 are each connected to one another through potentiostat electroanalyzer 326 via leads 320, 318, and 342 respectively.

According to the embodiment of the invention shown in FIG. 3, the contact portion of each channel of the test strip is the end of the strip to be inserted into the test or control mixtures.

Test mixture 308 is typically prepared, as described below, by combining a sample known or suspected to contain the analyte with the analyte analog-liposome conjugate and a binding material specific for the analyte in an aqueous, electrolytic medium. In accordance with the embodiment shown in FIG. 3, control mixture 309 is typically prepared to have the same concentration of the conjugate as test mixture 308, the same concentration of binding material as test mixture 308 and a known concentration of analyte in an electrolytic medium.

The electrolytic mixture containing the binding material, the conjugate, and the analyte (if present) is then incubated for a time sufficient to permit the conjugate and the analyte to compete with one another for binding with the binding material. The control mixture is similarly incubated. The incubation time will vary with the particular assay, however, in most cases, from about less than 1 minute to about 30 minutes will be sufficient to allow the competition reaction to reach or approach completion. Incubation times of from about 1 minute to about 30 minutes are easily achieved with the method of the invention, and are preferred, as one of the significant advantages of the present invention is the speed with which testing for analytes can be carried out. As one skilled in the art will appreciate, it is important that the competition reaction be permitted to approach completion, to avoid inaccurate results. However, it may be necessary to control the reaction time in some cases, because liposome-entrapping flocculants may form if the incubation period is too long.

Following incubation of the solution, the contact portion of absorbent material 312 of control channel D is inserted into control mixture 309, while the contact portion of absorbent material 312 of test channel E is inserted into test mixture 308. Wetting of absorbent material 312 by capillary action is allowed to continue at least until the electrochemical measurement portions in contact with first and second conductors 330 and 332, respectively, in channel D, and first and second conductors 334 and 336, respectively, in channel E are wet, (and preferably, until the solvent front reaches the end of the absorbent material) with control mixture 309 and test mixture 308, respectively. As control mixture 309 and test mixture 308 traverse channels D and E of the test device into and through liposome lysing portions 306d and 306e, the lipsomes of the conjugate are lysed to release the electroactive marker.

In this three electrode format, the potential of either the first or second conductor is controlled versus the reference electrode, and the potential of the other of the first or second conductors "floats" to maintain the same current through both of the electrodes. The magnitude of the current flowing between the first and second conductors is measured and correlated to the amount of the analyte, as the measured current is proportional to the marker ion concentration. By comparing the signal intensities in the electrochemical measurement portions defined by first and second conductors 330 and 332, respectively, in channel D, and first and second conductors 334 and 336, respectively, in channel E, the presence of an analyte at a level considered significant as, for example, exceeding a toxicity or regulatory limit represented by a tolerance level control in channel D, can be determined.

Although the reference electrodes are shown in FIG. 3 positioned between the contact portions of the channels and the liposome lysing portions, respectively, the reference electrode, if employed in either the competition or aggregation formats, can be positioned anywhere on the absorbent material between the end proximate to the contact portion and the electrochemical measurement portion defined by the interdigitated electrode array, including, for example, in the contact portion or liposome lysing portion. The reference electrode could even be placed in the test mixture if the mixture is kept in contact with the absorbent material during capillary traversal of the strip. Alternatively, the reference electrode could be placed on the back of the test strip or between the absorbent material and the backing support, as long as it is maintained in electrical contact with the interdigitated array. These and other configurations for the reference electrode and auxiliary electrode, which is discussed in greater detail below, will be apparent to those skilled in the art. It should also be noted that any of the two-, three-, and four-electrode systems described herein can be employed in both the competition and aggregation formats.

As was described above, devices in accordance with the aggregation embodiment of the invention can be constructed in single or multiple channel formats, depending on the desired application.

The support for the absorbent material where a support is desired or necessary will normally be hydrophobic, water insoluble, non-porous, and rigid, and usually will be of the same length and width as the absorbent strip but may be larger or smaller. A wide variety of organic and inorganic materials, both natural and synthetic, and combinations thereof, may be employed, provided only that the support does not interfere with the production of signal from the marker. Illustrative polymers include polyethylene, polypropylene, poly(4-methylbutene), polystyrene, polymethacrylate, poly(ethylene terephthalate), nylon, poly (vinyl chloride) poly(vinyl butyrate), glass, ceramics, metals, and the like.

The size of the piece of absorbent material is dependent on several considerations. For the aggregation embodiment of the invention, the primary consideration, as described further below, is to capture unaggregated conjugate at the measurement portion to give a sufficient signal so that a sensitive and accurate assay is achieved. The following discussion is primarily focused on strips of absorbent material for purpose of illustration and not limitation. As mentioned above, other shapes such as circular, oval, trigonal, and the like, fall equally within the scope of this invention. The dimensions thereof and other parameters can be determined by those skilled in the art with reference to the disclosure herein.

When capillary flow is predominantly upward, the length and thickness of the strip control the amount of mixture that can pass through the electrochemical measurement portion. If the transfer of a large volume of test mixture is desired, the fluid capacity of the strip above the electrochemical measurement portion must be sufficient to accommodate the desired volume. Alternatively, an absorbing pad or sponge may be used to contact the end of the strip opposite the end used to contact the test mixture. An absorbing pad or sponge may be used in this manner in situations when it is desirable to pull a larger volume of the test mixture across the test device.

To permit conservation of reagents and provide for samples of limited size, the width of the strip will generally be relatively narrow, usually less than 20 mm preferably less than 10 mm. Generally, the width of the strip will not be less than about 2 mm and will usually range from about 2 mm to 10 mm, preferably from about 3 mm to 6 mm.

As is described in detail below, the test device in accordance with the invention may be modified for simultaneous multiple analyte detection or determination. The length of the strip will depend on the concentration of the analyte and practical considerations such as ease of handling and the number of measurement portions on the strip and will be about 4 cm to 20 cm, usually about 5 cm to 15 cm, preferably about 6 to 13 cm but may be of any practical length. The structure of the strip can be varied widely and includes fine, medium fine, medium, medium coarse and coarse. In general, smaller pore size and finer material will provide slow capillary flow and more efficient capture of unaggregated conjugate on the strip. More significantly, an absorbent material having a smaller pore size will trap smaller aggregates. Courser, more porous materials provide faster flow, but the efficiency of capture is reduced. Selection of the porosity of the material depends on the rate of binding of the components for a given assay.

The position of the competitive binding or capture portions, and measurement portion (or portions, where a plurality of analytes are being determined), should be governed by the basic principle involved in the present invention. For example, in the competition embodiment, one desires to pass by capillarity a sufficient amount of the test mixture through the absorbent material to the electrochemical measurement portion to separate bound conjugate from unbound conjugate and to carry the unbound conjugate through the electrochemical measurement portion to produce a signal that is detectable. In this embodiment, it is desirable to position the electrochemical measurement portion close to the competitive binding portion. Desirably, the electrochemical measurement portion should be at least 3 mm, preferably at least 8 mm, from the competitive binding portion of the strip. The electrochemical measurement portion should be positioned on the absorbent material so as to enable the test solution to pass through the electrochemical measurement portion by capillary action. Generally, the distance between the competitive binding portion and the contact portion should be at least 2 mm, preferably at least 5 mm. Where several measurement portions are used for multi-analyte determinations, the measurement portions can be grouped close together or apart but must not be so close as to compromise resolution of the signals. Consequently, such measurement portions usually should be spaced not less than 0.5 mm apart, preferably at least 1 mm apart.

In carrying out the method of the invention, the protocol will normally involve combining the sample suspected of containing the analyte with the conjugate, for the competition embodiment, and, additionally, the binding material, in the aggregation embodiment, in an electrolytic aqueous medium to form an aqueous test mixture or solution. The sample may be derived from a wide variety of sources, such as physiologic fluids, illustrated by saliva, sweat, serum, plasma, urine, tear fluid, spinal fluid, etc., chemical processing streams, food, waste water, natural waters, soil extracts, etc. Various addenda may be added to adjust the properties of the test mixture, or of a carrier solution used as a wicking reagent, depending upon the properties of the other components of the device, as well as on those of the liposomes or the analyte analog-liposome conjugate, or the analyte itself. Examples of solution addenda which may be incorporated into test, control, or carrier solutions or mixtures in accordance with the invention include buffers, for example, pH and ionic strength, and sample or analyte solubilizing agents, such as, for example, nonpolar solvents.

The order of addition of the test sample (suspected of containing the analyte), the binding material (where appropriate), and the conjugate to one another is not critical. Generally, however, in the aggregation embodiment, it is preferred to allow the binding material and test sample to interact briefly before the addition of the conjugate to compensate for the competitive advantage enjoyed by the conjugate with its multiple binding material binding sites.

The contact portion of the absorbent material, which usually includes the end of the absorbent material to which the contact portion is proximate, is contacted with test mixture, usually by immersion of the contact portion into the test mixture. Wetting of the absorbent material by capillary action is allowed to continue at least until the measurement portion is wet, preferably until the solvent front reaches the end of the absorbent material opposite the first end.

Alternatively, the test mixture may be contacted with the absorbent material by spotting the test mixture (following incubation to form aggregates in the aggregation embodiment) onto the absorbent material in the contact portion. In this case, the contact portion includes a wicking portion at the first end of the absorbent material. In use, the wicking portion of the contact portion is inserted into a wicking reagent after the test mixture is spotted onto the contact portion, outside of the wicking portion.

For the most part, relatively short times are involved for the test mixture to traverse the strip. Usually, traversal of the test mixture over the strip will take at least 30 seconds and not more than ½ hour, more usually from about 1 minute to 10 minutes. In accordance with the method of the invention, the signal is rapidly, even immediately, detectable. Due to the relatively low flow rate induced by capillary action, there is ample time for redox cycling and increased sensitivity with the device and method of the invention.

The conjugate of the analyte analog and the marker-encapsulating liposome may be prepared by procedures generally known in the art, with the particular procedure used in a given case being dependent upon the analyte or analog which is employed. Such techniques include covalent coupling, derivatization or activation, and the like. The liposomes may be produced from a component which has been derivatized with the analyte, whereby the liposomes, when produced, are conjugated with the analyte. In another procedure, the liposomes, including the marker, may be initially formed, followed by conjugating the liposomes with the analyte or analyte analog by procedures known in the art.

Liposomes can be prepared from a wide variety of lipids, including phospholipids, glycolipids, steroids, relatively long chain alkyl esters; e.g., alkyl phosphates, fatty acid esters; e.g. lecithin, fatty amines, and the like. A mixture of fatty materials may be employed, such as a combination of neutral steroid, a charge amphiphile and a phospholipid. Illustrative examples of phospholipids include lecithin, sphingomyelin, and dipalmitoylphosphatidylcholine, etc. Representative steroids include cholesterol, chlorestanol, lanosterol, and the like. Representative charge amphiphilic compounds generally contain from 12 to 30 carbon atoms. Mono- or dialkyl phosphate esters, or alkylamines; e.g. dicetyl phosphate, stearyl amine, hexadecyl amine, dilaurylphosphate, and the like are representative.

The liposome sacs are prepared in aqueous solution containing the marker whereby the sacs will include the electroactive marker in their interiors. The liposome sacs may be prepared by vigorous agitation in the solution, followed by removal of the unencapsulated marker. Further details with respect to the preparation of liposomes are set forth in U.S. Pat. No. 4,342,826 and PCT International Publication No. WO 80/01515, both of which are incorporated by reference.

Because the conventional methods of liposome preparation (e.g., direct-injection and reverse-phase evaporation) involve organic solvents, proteins such as antibodies cannot be incorporated into the membrane bilayer without significant denaturation. To avoid this problem, a procedure has been developed that introduces the protein-lipid conjugate into the bilayer after formation of the liposomes by the conventional methods.

Normally, after the liposomes are formed, they are passed through a series of polycarbonate filters of successively smaller pore size (e.g., from 3 $\mu$m to 0.2 $\mu$m) to reduce lamellarity and size distribution. During this process, large multilamellar liposomes are presumably stripped of their outer lamellae which then reform to produce new, smaller unilamellar liposomes. It is this process that is taken advantage of in order to introduce the protein-lipid conjugate into the bilayer under more favorable aqueous conditions. Consequently, the protein-lipid conjugate, e.g., antibody-DPPE, is added to the liposome mixture prior to extrusion through the filters. This mixture is extruded numerous times (10 to 30 times is typical) to maximize insertion of the protein-lipid conjugate.

After extrusion, the procedure is again the same as the conventional method in which the liposomes are gel filtered and dialyzed to remove unencapsulated optical or electrochemical marker molecules.

Protein-lipid conjugate can be prepared by interaction of the amino group on the dipalmitoylphosphatidylethanolamine (DPPE) with different functional groups on the protein such as side chain amino or carboxyl groups via cross linkers known in the trade.

Conjugations between the DPPE and protein can also be accomplished by initially derivatizing the amino group of the DPPE with a maleimide group using cross linker such as maleimidobutyric acid N-hydroxysuccinimide ester and allowing it to react with thiol-containing proteins or a sulfhydryl group that is introduced into the protein via reagents such as 2-iminothiolane (Traut's reagent), SATA and SAMSA or by reduction of a disulfide cross linker such as SPDP and sulfo-LC-SPDP.

Glycoproteins such as antibody or receptors can be conjugated to DPPE through their carbohydrate moeity. This can be achieved by periodate oxidation of the vicinal hydroxyl groups on the carbohydrates to reactive aldehydes which in turn can react with a hydrazide bearing disulfide such as pyridyldithiopropionyl group. The amino group of the DPPE can be derivatized with a maleimide group as mentioned previously and allowed to react with the sulfhydryl group generated by reduction of the disulfide group on the modified glycoprotein.

As hereinabove indicated, the signal producing system includes an electroactive marker included in the interior of the conjugated liposomes. Suitable markers are those which are electrochemically active but will not degrade the liposomes or otherwise leach out of the liposomes. They include metal ions, organic compounds such as quinones, phenols, and NADH, and organometallic compounds such as derivatized ferrocenes. Ferrocyanide is the most preferred electroactive marker in accordance with the invention.

The use of liposomes as described in the present application provides several advantages over traditional signal production systems employing, for example, enzymes. These advantages include increased signal intensity, shelf stability, and instantaneous release of signal-producing markers, as described in T. A. Siebert, S. G. Reeves, R. A. Durst, *Analytica Chimica Acta* 282, 297–305 (1993); W. T. Yap, L. Locascio-Brown, A. L. Plant, S. J. Choquette, *Analytical Chemistry* 63, 2007 (1991); A. L. Plant, M. V. Brizgys, L. Locasio-Brown, R. A. Durst, *Analytical Biochemistry* 176, 420–426 (1989); L. Locascio-Brown, A. L. Plant, V. Horvath, R. A. Durst, *Analytical Chemistry* 62, 2587–2593 (1990); and R. A. Durst, L. Locascio-Brown, A. L. Plant, R. D. Schmid, Eds., *Flow Injection Analysis based on enzymes or antibodies*, vol. 14 (VCH, Weinheim, 1990), each of which is hereby incorporated by reference. For example, initial calculations indicate that the rupture of a single liposome in a typical capillary electrophoresis sample volume would lead to a concentration of 5 $\mu$M $K_4Fe(CN)_6$ at the interdigitated electrode array detector. Therefore, due to the great sensitivity of the interdigitated electrode arrays, the detection of single liposome events should be theoretically possible with the present system.

As described above, a liposome lysing agent is bound directly to the absorbent material. Suitable liposome lysing materials include surfactants such as octylglucopyranoside, sodium dioxycholate, sodium dodecylsulfate, polyoxyethylenesorbitan monolaurate sold by Sigma under the trademark Tween-20, and a non-ionic surfactant sold by Sigma under the trademark Triton X-100, which is t-octylphenoxypolyethoxyethanol. Octylglucopyranoside is a preferred lysing agent for many assays, because it lyses liposomes rapidly and does not appear to interfere with signal measurement. Alternatively, complement lysis of liposomes may be employed.

In the competition embodiment of the invention, a conjugate of an analyte analog and marker-loaded liposomes are combined in an electrolytic aqueous medium with a sample suspected of containing the analyte, to provide an aqueous test composition. Alternatively, the combination of the conjugate and the sample suspected of containing the analyte can take place on the absorbent material. The primary consideration is that a test solution containing the sample come in contact with a conjugate of the analyte and the marker-loaded liposomes prior to or at the contact portion of the absorbent material. The binding material is bound to the absorbent material between the electrochemical measurement portion and the contact portion. The contact portion of the absorbent material is contacted with the test solution, which will traverse the absorbent material through capillary action. This transversal can be upward, downward, horizontal or combinations thereof.

The competition embodiment provides for an immunoseparation of bound conjugate from unbound conjugate. This is accomplished by having the binding material bound to the absorbent material in the competitive binding portion between the electrochemical measurement portion and the contact portion. A binding material will normally be chosen that provides for direct binding to the analyte. Usually, the binding material will be present in an amount that will provide the appropriate sensitivity required for a specific analyte.

In the aggregation format of the invention, a conjugate of an analyte analog and marker-loaded liposomes are combined in an aqueous, electrolytic medium with a sample suspected of containing the analyte and a binding material specific for the analyte, to provide an aqueous test mixture. The liposomes incorporated in the conjugate have multiple analyte analog molecules bound hereto and, therefore, multiple binding sites for the binding material. In the absence of the analyte, binding material will react exclusively with the conjugate, resulting in the formation of relatively large aggregates, each of which may include multiple liposomes (see, for example, the two examples of conjugate-binding material aggregates in FIG. 5B). During migration of the test mixture across the test device, the large aggregates formed during the incubation will tend to be retained in the interstices of the nitrocellulose matrix and will form an "aggregation zone" on the absorbent material, usually at or near the meniscus of the test mixture when the device is inserted as shown in FIG. 3 into the test mixture. By occupying binding sites on the binding material, the analyte inhibits conjugate aggregation. Thus, the greater the concentration of analyte in the test sample, fewer aggregates will form and those that do form will be relatively limited in size. Smaller particles, including unaggregated liposome-analyte analog conjugate, will not be retained at the "aggregation zone" and will continue to migrate through the electrochemical portion. The conjugates that do not aggregate will be proportional to the amount of analyte in the mixture, and will release their marker to produce a signal in the electrochemical measurement portion.

The aggregation embodiment thus also provides for an immunoseparation of aggregated conjugate from unaggregated conjugate. This is accomplished as a result of the inability of aggregated conjugate to proceed beyond a certain position on the absorbent material.

The movement of the test mixture along the absorbent material is due to capillary action. This capillary movement along the absorbent material causes the test mixture to be carried to and through the electrochemical measurement portion, where measurement of the marker released from the liposomes takes place.

An electroactive species, such as ferrocyanide, is encapsulated in the liposomes. Electrodes are printed onto the strip, or the strip is placed in contact with reusable electrodes. After lysis of the liposomes, the quantity of the electroactive species is determined.

The reference electrode, if employed, will usually be a silver electrode, although lead may alternatively be used for the reference electrode. The electrodes forming the interdigitated array may be prepared from any suitable materials such as the noble metals, other metals such copper and zinc, or carbon electrode materials in various forms, including graphitic, glassy and reticulated carbon materials, or suitable mixtures of these materials. The first conductor may be composed of the same or a different material from the second conductor.

The electrochemical detection system of the present invention comprises an interdigitated set of microelectrodes, and, optionally, a reference electrode. In another optional embodiment, a "four-electrode" system comprising the interdigitated array, a reference electrode, and an auxiliary electrode can be employed. A four-electrode system is described in O. Niwa, M. Morita, H. Tabei, Anal. Chem. 62, 447–452 (1990). Platinum is a suitable material for the auxiliary electrode.

The interdigitated electrode set can be fabricated on a support, such as a thermally oxidized silicon wafer by photolithography and the lift off technique described in Aoki, A; Matsue, T.; Uchida, I. Analytical Chemistry 1990, 62, 2206–10, which is hereby incorporated by reference. See also K. Aoki, M. Morita, O. Niwa, H. Tabei, Journal of Electroanalytical Chemistry 256, 259 (1988) and Aoki, A. M., Tomokazu; Uchida, Isamu, Analytical Chemistry 1990, 62, 2206–10, which are also hereby incorporated by reference. Platinum interdigitated electrodes are preferably formed by sputter deposition and the lift-off technique described by Aoki. Silver lead patterns, and a platinum electrode and silver reference electrode, if used, are preferably formed by photolithography and the lift-off technique. If possible, all lead wires, preferably composed of silver, should be located distal to the surface of the interdigitated array.

Electrodes as described herein have been fabricated at the National Nanofabrication Facility (Ithaca, N.Y.). Separate photomasks were drawn for silver and platinum materials.

The electrode set formed on the silicon wafer can then be applied directly to the surface of the absorbent material. Borosilcate glass and quartz substrates may alternatively be employed. Such substrate-backed electrodes can be removed from the strip after the assay is complete and prepared for re-use if desired. If electrodes are to be re-used, it is often preferable to coat them with a protective polymer layer. Agarose, for example, can be used to prevent passivation of electrodes.

In a preferred embodiment, each electrode set has an overall size of 9×4 mm and is approximately 350 $\mu$m thick.

The actual area of interdigitation is 6 mm×1 mm and is designed to fit conveniently across 5 mm wide immunomigration strips. This arrangement allows for the array to completely straddle the absorbent material, maximizing the interaction of electroactive marker with the electrodes, and, therefore, assay sensitivity. A preferred interdigitated array consists of 125 pair of 3 $\mu$m wide microelectrode fingers separated by a 1–5 $\mu$m gap. Preferred reference and auxiliary electrodes are 7×1 mm.

Although the preferred configuration is described above, the first conductor and said second conductor may comprise from 2 to 500 fingers, and the fingers of said first and second conductors can range in size from about 1 $\mu$m to about 20 $\mu$m wide. The electrode fingers can be spaced from about 0.5 $\mu$m to about 10 $\mu$m apart.

Each of the electrodes shown in FIGS. 1 and 3 may alternatively be prepared by screen printing of the electrode materials onto the absorbent material, although with screen printing, the interelectrode distance may be as much as 50 $\mu$m. As is well known, screen printing involves preparation of an organic or aqueous slurry of the electrode material, typically, a fine powder of carbon, gold, etc., followed by application of the slurry across and through a silk screen onto the absorbent material of the test device. This slurry may optionally include a polymeric binder which aids in aggregating the fine metallic particles together on the surface of the absorbent material. The electrode material slurry may be fixed on the surface of the absorbent material by heating, however, the printed electrode portions are preferably allowed to air dry on the surface of the absorbent material.

The test mixture and any control mixtures are electrolyte solutions such as saline solutions of the analyte and analyte analog-liposome conjugate, and, for the aggregation embodiment, the binding material.

Devices which may be used as potentiostats in accordance with the invention include the Cypress (Lawrence, Kans.) System Electrochemical Analyzer (CS-1090) and the BAS (West Lafayette, Ind.) Amperometric Detector (LC-4C).

The solvent for the test solution will normally be an aqueous medium, which may be up to about 40 weight percent of other polar solvents, particularly solvents having from 1 to 6, more usually of from 1 to 4, carbon atoms, including alcohols, dimethylformamide and dimethylsulfoxide, dioxane and the like. Usually, the cosolvents will be present in less than about 20 weight percent. Under some circumstances, depending on the nature of the sample, some or all of the aqueous medium could be provided by the sample itself.

The pH for the medium will usually be in the range of 4–10, usually 5–9, and preferably in the range of about 6–8. The pH is chosen to maintain a significant level of binding affinity of the binding members and optimal generation of signal by the signal producing system. Various buffers may be used to achieve the desired pH and maintain the pH during the assay. Illustrative buffers include borate, phosphate, carbonate, tris, barbital and the like. The particular buffer employed is usually not critical, but in individual assays, one buffer may be preferred over another.

The concentration of electrolytes in the medium will usually be adjusted to achieve isotonicity or equi-osmolality with the solution in the interior of the liposomes to prevent their crenation or swelling.

With some increased complexity of the excitation waveform applied by the electroanalyzer, electrochemical measurement in accordance with the invention may also be carried out using stripping voltammetry, employing, for example, liposome encapsulated metal ions for detection and measurement.

Moderate, and desirably substantially constant, temperatures are normally employed for carrying out the assay. The temperatures for the assay and production of a detectable signal will generally be in the range of about 4–45° C., more usually in the range of about 10–38° C., and frequently, will be ambient temperatures, that is, about 15–25° C.

The concentration, in the liquid sample, of analyte which may be assayed will generally vary about $10^{-3}$ to about $10^{-15}$M, more usually from about $10^{-5}$ to $10^{-10}$M. Considerations such as the concentration of the analyte of interest and the protocol will normally determine the concentration of the other reagents.

With the test devices and methods of the invention, one may also assay a test sample for a plurality of analytes such as toxic chemicals, or screen for one or more of a plurality of analytes. In one embodiment, the test device includes multiple sets of interdigitated electrode arrays. By appropriately controlling the potentials at the electrodes, different marker ions can be measured and referred back to separate analyte concentrations. In another embodiment, a single set of electrodes, preferably in a three-electrode configuration as shown and described above with reference to FIG. 3, can be used. The potential is varied, for example, by scanning linearly with time, to produce currents proportional to the different ion concentrations at unique potentials (times).

As a matter of convenience, the present device can be provided in a kit in packaged combination with predetermined amounts of reagents for use in assaying for an analyte or a plurality of analytes. Aside from the absorbent test device and the analyte analog-liposome conjugate, and, where appropriate, the binding material, other additives such as ancillary reagents may be included, for example, stabilizers, buffers, and the like. The relative amounts of the various reagents may be varied widely, to provide for concentration in solution of the reagents which substantially optimizes the sensitivity of the assay. The reagents can be provided as dry powders, usually lyophilized, including excipients, which on dissolution will provide for a reagent solution having the appropriate concentrations for performing the assay. The kit or package may include other components such as standards of the analyte or analytes (analyte samples having known concentrations of the analyte).

The present invention is applicable to procedures and products for determining a wide variety of analytes. As representative examples of types of analytes, there may be mentioned: environmental and food contaminants, including pesticides and toxic industrial chemicals; drugs, including therapeutic drugs and drugs of abuse; hormones, vitamins, proteins, including antibodies of all classes; peptides; steroids; bacteria; fungi; viruses; parasites; components or products of bacteria, fungi, viruses, or parasites; allergens of all types; products or components of normal or malignant cells; etc. As particular examples, there may be mentioned $T_4$; $T_3$; digoxin; hCG; insulin; theophylline; leutinizing hormones and organisms causing or associated with various disease states, such as streptococcus pyrogenes (group A), Herpes Simplex I and II, cytomegalovirus, chlamydiae, etc. The invention may also be used to determine relative antibody affinities.

As hereinabove indicated, the assay may be qualitative (presence or absence of certain level of analyte) or quantitative or semi-quantitative. The preparation of suitable standards and/or standard curves is deemed to be within the scope of those skilled in the art from the teachings herein.

The method of the invention, and preparation and use of the test device in accordance with the invention, are illustrated by the following Examples.

EXAMPLES

In these Examples, the "competition" and "aggregation" embodiments identified above are referred to as the "liposome-immunocompetition (LIC)" and the "liposome-immunoaggregation (LIA)" formats or devices, respectively. References to "IDA" or "IDAs" are to the interdigitated electrode arrays of the present invention.

Materials for Examples 1–6

Dipalmitoyl phosphatidyl ethanolamine (DPPE), cholesterol, Tween-20, triethylamine, tris(hydroxymethyl) aminomethane (Tris), and potassium ferrocyanide ($K_4Fe(CN)_6$) were purchased from Sigma Chemical Co. (St. Louis, Mo.). Dipalmitoyl phosphatidyl choline (DPPC) and dipalmitoyl phosphatidyl glycerol (DPPG) were obtained from Avanti Polar Lipids, Inc. (Alabaster, Ala.). Biotin-x-DPPE was purchased from Molecular Probes (Eugene, Oreg.). The 2-chlorophenyl benzoic acid (2-ClPB) was supplied by the General Electric Corp. (Schenectady, N.Y.). Silicon dioxide wafers can be obtained from several commercial sources, however in the present example they were prepared by standard methods at the National Nanofabrication Facility, Cornell University (NNF). All electrode materials and supplies are also supplied at the NNF, but can be obtained from many commercial sources.

EXAMPLE 1—Fabrication and Use of Interdigitated Microelectrode Arrays

Each IDA electrochemical detector presented in this example consists of 125 pairs of 3 $\mu$m wide ultramicroelectrode fingers separated by a 1 $\mu$m gap. Each electrode finger is 6.2 mm long and is interdigitated with opposing fingers for 6 mm as shown in FIGS. 1–3. These IDAs were fabricated at the National Nanofabrication Facility under clean room conditions, as described in Niwa, O.; Tabei, H. Analytical Chemistry 1994, 66, 285–289. This design was modified for the present invention by increasing the total number of fingers and extending the area of interdigitation. The flowing immunochromatographic test-strip provides a very small diffusional environment as well as the possibility of concentrating substances at the detector over time. Furthermore, the increased number and closer proximity of the electrode pattern was done to further enhance analytical sensitivity and the extended area of interdigitation is created specially to interface with the previously developed 5 mm wide immunochromatographic strips, which are described in Siebert, T. A.; Reeves, S. G.; Durst, R. A. Analytica Chimica Acta 1993, 282, 297–305; Siebert, S. T. A.; Reeves, S. G.; Roberts, M. A.; Durst, R. A. Analytica Chimica Acta 1995, 311, 309–318; and Roberts, M. A.; Durst, R. A. Analytical Chem 1995, 67, 482–491, and U.S. patent applications Ser. Nos. 08/135,741 and 08/382,482, all of which is hereby incorporated by reference. This design allows for a 1 mm overlap which is important for their ease of use under non-laboratory settings.

A 10 fold enlarged positive IDA pattern was initially generated on a chrome substrate, creating a "photomask" by standard development processes, described in Aoki, A. M., Tomokazu; Uchida, Isamu Analytical Chemistry 1990, 62, 2206–10, hereby incorporated by reference. The IDA pattern was then built on photoresist-coated thermally-oxidized silicon wafer. The 10 fold enlarged photomask pattern is used to expose the coated wafer to ultraviolet (UV) radiation in a step and repeat pattern. In the present example 14 devices were created on a standard 3.5 inch wafer. The photoresist which is exposed to the UV light becomes soluble in a commercially available development solution. This solution was used to remove the photoresist only within the desired IDA pattern.

Platinum IDA ultramicroelectrodes were formed by sputter deposition and the lift off technique as described by Aoki, A. M., Tomokazu; Uchida, Isamu Analytical Chemistry 1990, 62, 2206–10. These techniques are generally known to those skilled in the art of micro- and nanofabrication and are hereby incorporated by reference. Briefly the techniques comprise the following steps: a) the desired electrode metal (here platinum was used, but silver, gold, chrome, titanium, etc. can also be used) is placed in an ultra high vacuum (UHV) chamber and then heated with a filament or electron gun; b) First a metal with high adhesion to the wafer and then the electrode metal is sputtered onto the photoresist-patterned silicon-dioxide wafer, forming a thin film across its surface; c) The metal coated wafer is then removed from the UHV chamber and immersed in a solution of a suitable solvent (acetone being used with a Shipley positive photoresist in the present invention); d) The photoresist being soluble in the solvent "lifts off", along with the metal coating, into the solution and subsequently falls to the bottom of the container (the metal-coating which is adherent directly to the wafer is stable in this solution and remains creating the desired IDA pattern); e) The patterned wafer is then rinsed under distilled water, dried, and cut into individual IDA test devices using a diamond-tipped scribing device.

After fabrication, electrodes were tested for shorts and used only if the resistance across the IDA was greater than 1 M½. Electrochemical measurements were made using a suitable electrochemical test station. In this example a Cypress (Lawrence, Kans.) CS-1090 computer controlled electroanalytical system was used.

EXAMPLE 2—Examination and Characterization of Arrays

Figure 6A:
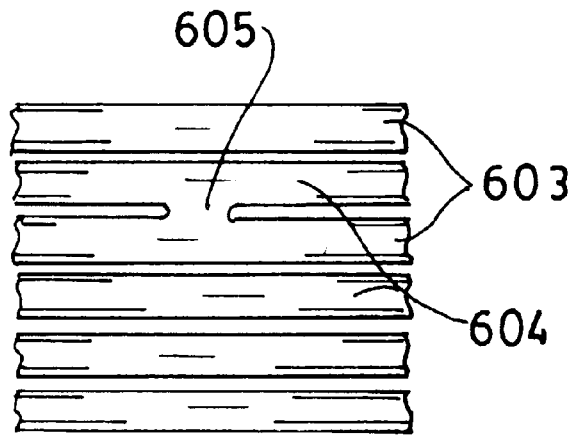
FIGS. 6*a* and 6*b* are schematic views of electrode fingers fabricated in accordance with the invention shown before (FIG. 6*a*) and after (FIG. 6*b*) repair of a short.
Figure 6B:
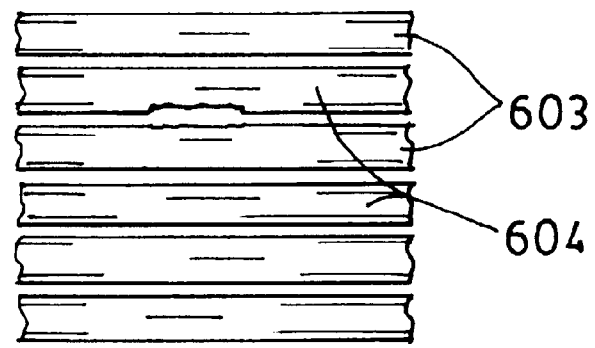

After production the interdigitated arrays were examined by both light and electron microscopy. Both top and side views were examined in order to better understand the true nature of the interdigitated array-immunoassay interface. Also, the number of shorts and breaks were determined by measuring the electrical resistance both along and between electrode finger sets. Almost 80% of the arrays had a resistance less than 10k$\Omega$, across the two platinum finger sets, and were not immediately acceptable for use. Shorts could be visually observed using light microscopy and their exact locations were noted. Interdigitated arrays possessing fewer than 4 shorts per device were then taken through a repair step using a focused ion beam milling technique. The complete removal of one such short is shown schematically in FIGS. 6a and 6b. Short 605 between one pair of fingers 604 and 603 is shown in FIG. 6a. The same set of electrode fingers is shown in FIG. 6b following removal of the short as described above. If all such shorts were removed using this technique the resistance across the array greatly increased. Therefore if a higher array fabrication yield is desired this technique may be used to rescue devices that are initially unacceptable. Roughly 20% of fabricated arrays initially had a resistance greater than 1 M$\Omega$ and were deemed acceptable for further use.

Figure 4A:
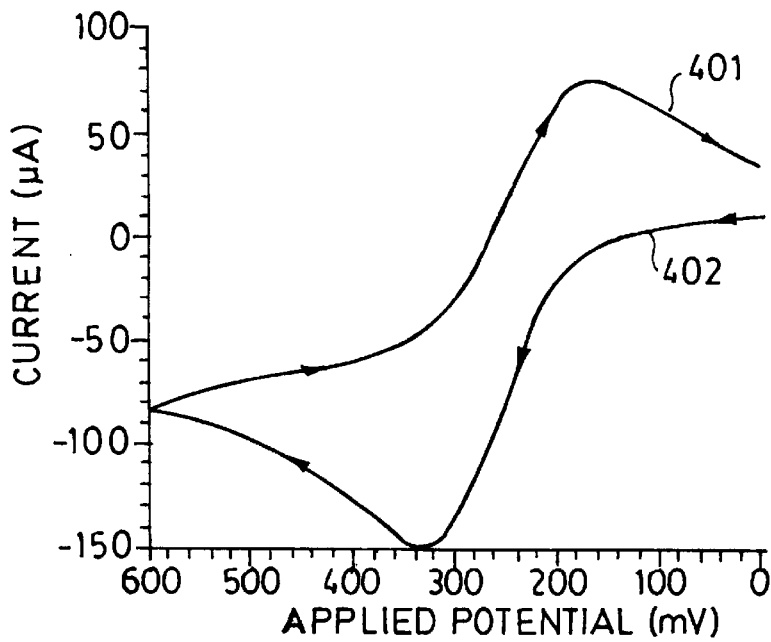
FIG. 4 shows cyclic voltammograms for standard electrode (FIG. 4A) and interdigitated electrode array (FIG. 4B) configurations.
Figure 4B:
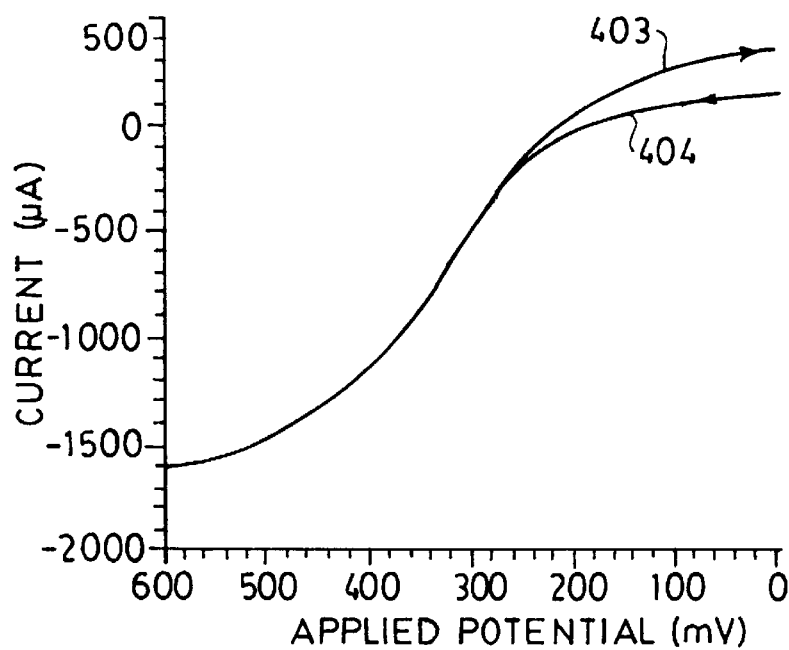

For purposes of electrochemical characterization, small microwells were created over the interdigitated electrode array surface with commercially available food tubing and a chemically inert epoxy. Microwells may contain up to 50 $\mu$L of sample and can be conveniently washed after analysis. FIGS. 4a and 4b show cyclic voltammograms of 50 mM $K_4Fe(CN)_6$ for an interdigitated array-microwell device used both in a conventional (MACRO mode) (FIG. 4a) and an interdigitated configuration (FIG. 4b). The MACRO mode configuration consisted of applying a potential across only one finer set and the large auxiliary electrode. Due to the 100 $\mu$m spacing between these two structures little advantage over is conventional ultramicroelectrodes is expected. The interdigitated array mode configuration involved applying a potential across the two finger sets and therefore, takes full advantage of the electrochemical advantages already discussed.

A cyclic voltammogram (CV) conducted in MACRO mode, as described above, is shown in FIG. 4a. A conventionally shaped CV is observed with characteristic oxidation and reduction potentials. It can be seen that the shape of the CV generated by the device used in the interdigitated array configuration (FIG. 4b) has changed significantly. This is because the current generated from the test solution at any given applied voltage is not diffusionally limited. It can also be seen that the maximum current obtained through a single scan is on the order of 300 times greater in the interdigitated array mode. This is due to the close approximation of cathodic and anodic finger sets which allows individual molecules to shuttle back and forth between finger sets and participate in redox cycling. Therefore, devices used in the interdigitated array mode enhance the sensitivity or limiting current obtained at a given applied voltage, which is clearly seen in FIG. 4b. These experimental observations confirm that the microfabricated interdigitated arrays are performing as expected and that advantageous applications to immunoassays can be expected.

EXAMPLE 3—Marker-Encapsulating Analyte-Tagged Liposomes

An electrolytic carrier solution, used both in the preparation of liposomes as well as in the assay protocol, was composed of a highly conductive Tris-HCL buffer with saline (TBS: 20 mM Tris-HCL, 100 mM NaCl, 0.01% sodium azide, pH 7.0). The electrochemical marker, $K_4Fe(CN)_6$ was dissolved in TBS, to a final-concentration of 200 mM, prior to liposome preparation.

Liposomes were designed to be competitive markers in immunomigration analysis by incorporating previously coupled alachlor-DPPE into liposome bilayers by the reverse-phase evaporation method, described in Siebert, T. A.; Reeves, S. G.; Durst, R. A. Analytica Chimica Acta 1993, 282, 297–305; Siebert, S. T. A.; Reeves, S. G.; Roberts, M. A.; Durst, R. A. Analytica Chimica Acta 1995, 311, 309–318; and Roberts, M. A.; Durst, R. A. Analytical Chem 1995, 67, 482–491. This was accomplished by dissolving a total of 85 $\mu$mole of a phospholipid mixture consisting of DPPC, cholesterol, DPPG, alachlor-DPPE conjugate, and biotin-x-DPPE in a molar ratio of 5:5:0.5:0.1:0.01 in a 4.2 mL solvent solution of 1:1 chloroform:methanol (v/v) at 45° C. A small aliquot (1.4 mL) of the 200 mM $K_4Fe(CN)_6$ solution was added to the lipid-carrying solvent phase and then agitated by sonication for 1 min, resulting in an emulsion. The solvent phase was then evaporated from the emulsion with a rotating evaporator, inducing the spontaneous formation of liposomes, as described in Szoka, S.; Olsen, F.; Heath, T.; Vail, W.; Mayhew, E.; Papahadjopoulos, D. Biochimica et Biophysica Acta 1980, 601, 559–571, hereby incorporated by reference.

After all solvent was removed and only a thin, oily film remains an additional 2.6 mL of the $K_4Fe(CN)_6$ solution was added with gentle swirling. This liposome-containing solution was then passed through a series of polycarbonate filters of 3, 0.4, and 0.2 μm diameter pore sizes. Marker-encapsulating liposomes were finally separated from any remaining free marker in solution by dialysis in 1 L of TBS, with at least three changes of solution.

Liposomes prepared by the reverse phase process have been noted to have high aqueous space to lipid ratios, efficiently capturing large amounts of the original aqueous phase (see Szoka, F., Jr.; Papahadjopoulos, D. Annual Reviews in Biophysics and Bioengineering 1980, 9, 467–508, hereby incorporated by reference); in this example the electrochemical marker, $K4Fe(CN)_6$ dissolved in TBS. The reverse phase evaporation process is also known in the literature to produce largely unilamelar bilayer vesicles in the size range of 0.1 to 1 μm in diameter, as described in New, R. R. C. In Practical Approach Series; Rickwood, D., Hames, B. D., Eds.; Oxford University Press: New York, 1990, pp 301, hereby incorporated by reference. Liposome preparations produced by the method presented in this example are typically observed to have diameters of approximately 0.3 +/−0.09 μm as measured by laser diffraction particle size analysis in a Coulter LS 130 instrument (Coulter Corporation, Hialeah, Fla.) using the manufacturer's method.

EXAMPLE 4—Liposome Lysis

Total and almost instantaneous lysis of the liposomes can be effected by addition of the surfactant Triton X-100 at a final concentration of 1% (v/v) or more in a liposome test solution at room temperature. Many other detergents should also be suitable for liposome lysis which include but are not limited to; Triton X-100, Span 20, Nonindet P-40, CHAPSO, n-octyl-b-D-glucopyranoside, Tergitol, Tween 20, deoxycholate, Brij 30, Bridj 52, Triton X-100 (reduced), polyoxyethylene ether W1 and Tween-20. In the present invention Triton X-100 was found to produce the lowest background signal during electrochemical detection and is, therefore, used in all experimental protocol described here.

Detergent lysis may be performed in two ways. If liposome-based IDA-detectable assays, either for developmental purposes or as actual tests, are to be performed in microwells then a 1% solution of detergent is simply added to test wells after liposome-analyte competition occurs. Liposomes will subsequently lyse, releasing $K_4Fe(CN)_6$, which can then be measured with an IDA electrochemical detector as described below in Example 6.

In a preferential embodiment of the present invention, a highly concentrated detergent solution (50% v/v) is applied directly to an immunochromatographic membrane using brushes, swabs, or spraying devices such as the Linomat IV (CAMAG Scientific Inc., Wrightville Beach, N.C.) microprocessor controlled TLC sample applicator which has been previously used in our laboratory for the application of various protein receptor solutions to immunochromatographic test devices. The key criteria for such a spraying device are reproducible spraying of protein-based solutions in narrowly defined zones (preferably less than 5 mm) and constant table motion at roughly 10 mm $sec^{-1}$. The device thereby sprays solutions onto nitrocellulose sheets moving underneath the spray nozzle at a constant rate.

The location and time of application of this surfactant zone is described below in Example 5. The surfactant zone, as well as all other zones on the test device, are dried prior to use. Therefore during use, $K_4Fe(CN)_6$-encapsulating liposome reagents moving along the test strip by capillary action will encounter a large amount of surfactant directly over detergent zones, as shown in FIGS. 1 and 3. This configuration allows for site-specific liposome lysis and subsequent release of electrochemically active markers such as $K_4Fe(CN)_6$. Once released markers will continue to migrate by capillary action and eventually pass the IDA where electrochemical detection may occur. It should be stressed that marker release occurs in the same small diffusional environment, defined by the small pores of the immunochromatographic support membrane, that subsequent electrochemical detection will operate. This means that very little dilution of the 200 mM $K_4Fe(CN)_6$ will occur prior to detection and will correspond to high detector sensitivity to the liposome reagent, which is the key to the biochemical detection of analyte-receptor binding.

EXAMPLE 5—Preparation of Inmunochromatographic Sensor Strips for use with IDA Electrochemical Detection Immunochromatographic test strips generally consist of some polymer substrate of a particular pore size, which is adherent to a plastic backing, providing rigidity and physical stability to the resulting test device. In the present non-limiting example, plastic-backed nitrocellulose with a mean pore size of 0.45 μm is used. The nitrocellulose membrane is cut into 8×15 cm sheets, thoroughly wetted with 10% methanolic TBS, pH 7.0, and dried under a vacuum. These smaller membrane sheets are mounted on a Linomat IV (CAMAG Scientific Inc., Wrightville Beach, N.C.) microprocessor controlled TLC sample applicator. In the case of the liposome-immunocompetition device (LIC), solutions of anti-analyte antibodies (approximately 0.2 mg mL-1) and surfactant (approximately 50% v/v) are applied at 1.25 μL s-1, for 85 s, with 190 kPa (27.5 psi) N2 producing zones at 1 and 2 cm from the bottom, as shown in FIG. 1. In the case of the liposome-immunoaggregation device, the aggregation is self-forming, and therefore, only the surfactant zone is applied at this stage. Sheets designed for both formats, are vacuum dried for 1.5 h. The coated nitrocellulose sheet is immersed in the blocking agent (0.25–0.75% gelatin, 0.02% PVP, 0.005% CNDM, 0.002% Tween-20) for 1 h on a rotating mixer and dried under vacuum for 3–4 h. Prepared sheets are finally cut into 0.5×8 cm test strips and stored in the presence of silica gel desiccant at either room temperature or 4° C. until ready for use.

EXAMPLE 6—Assay Protocol IDA-Sensor Strip Operation

For either the LIC or LIA formats an IDA electrochemical detector, prepared as above, is first attached to an immunochromatographic test strip. The IDA detector can be simply held in contact with the test strip at 4 cm or higher above the bottom with any simple clip or small device exerting pressure on the detector-strip interface. Commercially available spring loaded clips (office supplies) are used in the description of the present example, although any number of holders, clamps, vices, etc. can be envisioned for this purpose. It is sufficient for successful completion of the assay that only contact is made, that the 5 mm wide test strip is held somewhere within the 6 mm of inderdigitation, and that the IDA does not move during detection.

The assay using the LIC format, shown in FIG. 1, consists of a solution containing an unknown sample, analyte analog-tagged liposomes, a nitrocellulose test strip (immobilized anti-analyte and surfactant zones in sequence), and an IDA electrochemical detector. The LIC assay is initiated by dispensing 25 μL of the sample (in water or up to 30% methanol extraction solvent) and 25 μL of a 3 times concentrated solution of TBS buffer into a 10×75 mm glass test tube, mixing the contents, and then adding 25 μL of a liposome solution (approximately 4×104 liposomes μL-1, 200 mM encapsulated $K_4Fe(CN)_6$).

The method for the LIA assay, shown in FIG. 3, is modified by adding approximately 30 picomoles of anti-analyte antibody per drop to the concentrated TBS solution. Furthermore, after mixing, the solution is allowed to incubate at room temperature for 15 min before continuing with the assay. After these initial preparations the test tube is shaken mildly to mix the contents before inserting the test strip.

For both techniques, the IDA-test strip couple is put into contact with the reaction solution in order to initiate flow by capillary action. It should be appreciated by those skilled in the art that depending on the desired test device clamp/holder system, capillary flow may be initiated in either a horizontal or vertical configuration. One possible configuration utilizing horizontal flow is a test strip holder, as shown in co-pending application Ser. Nos. 08/135,741 and 08/382,482. After flow is initiated, an electrochemical potential is applied to the two-electrode configuration of the IDA that is just sufficient to oxidize $K_4Fe(CN)_6$ (+330 mV) or any other desired electrochemical marker that may be encapsulated in liposomes. At this initial time no solution is in contact with the IDA and, therefore, there will be no current measured.

Analyte-tagged liposomes will undergo competition for a limited number of antibody-binding sites, by either the LIC or LIA mechanisms as described earlier, and an inversely proportional number of liposomes will be bound at either the antibody or aggregation zones respectively. An analyte-proportional number of liposomes will escape this zone and subsequently encounter the surfactant lysis zone. After lysis, liposome-released $K_4Fe(CN)_6$ continues to move by capillary action to the detection zone, approximately 4 cm from the bottom, where the IDA is held in contact with the test strip. When the test solution comes into contact with the polarized set of interdigitated electrodes, $K_4Fe(CN)_6$ will quickly be oxidized due to the ultramicroelectrode behavior of the IDA as well as the small diffusional space of the nitrocellulose test-strip. Furthermore, REDOX cycling may occur due to the close approximation of cathode and anode and the good reversibility of the $K_4Fe(CN)_6$ marker. At this point current between the anode and cathode can immediately be monitored and integrated over time. Due to the fact that a circuit between the interdigitated electrode sets is initiated by the capillary flow, the assay will be essentially self-timing. The amount of current measured amperometricly at the IDA should be directly proportional to the amount of analyte in the original test solution.

After completion of the assay, both the test strip and IDA detector module may be discarded. If desired, the IDA can be cleaned with a suitable solvent and reused, although the current embodiment envisions a truly disposable technology with no interference from previous analyses.

Although the invention has been described in detail for the purpose of illustration, it is understood that such detail is solely for that purpose, and variations can be made therein by those skilled in the art without departing from the spirit and scope of the invention which is defined by the following claims.

What is claimed is:

1. A test device for detecting or quantifying an analyte in a test sample, said test device comprising an absorbent material, said absorbent material comprising:
   a contact portion at or proximate to a first end of said absorbent material;
   an electrochemical measurement portion at a location on said absorbent material which is positioned away from the first end, wherein said electrochemical measurement portion comprises an electrochemical detector cell consisting of a first conductor comprising a plurality of fingers disposed on said absorbent material and a second conductor comprising a plurality of fingers disposed on said absorbent material, wherein said fingers of said first conductor are interdigitated with said fingers of said second conductor, and wherein said conductors induce redox cycling; and
   a liposome lysing portion segregated from said contact portion and having a liposome lysing agent bound thereto, wherein said liposome lysing portion either is positioned between said contact portion and said electrochemical measurement portion, or partially or completely coincides with said electrochemical measurement portion.

2. A test device according to claim 1, wherein said absorbent material further comprises a competitive binding portion positioned between and segregated from said contact portion and said liposome lysing portion and having a binding material for the analyte bound to said competitive binding portion.

3. A test device according to claim 2, further comprising a reference electrode disposed on said absorbent material between said competitive binding portion and said electrochemical measurement portion.

4. A test device according to claim 3, wherein said reference electrode is electrically connected to said first conductor and said second conductor.

5. A test device according to claim 2, wherein said binding material is present in said competitive binding portion in a concentration of at least 1 μg/cm$^2$ absorbent material.

6. A test device according to claim 1 or 2, wherein said first conductor and said second conductor are electrically connected to one another.

7. A test device according to claim 1 or 2, further comprising a support material on which said absorbent material is mounted.

8. A test device according to claim 1 or 2, wherein said absorbent material is nitrocellulose.

9. A test device according to claim 8, wherein said nitrocellulose has a pore size of from 0.05 μm to about 50 μm.

10. A test device according to claim 1 or 2, wherein said contact portion further comprises a wicking portion at said first end.

11. A test device according to claim 1 or 2, wherein said absorbent material has been treated with one or more blocking agents, surfactants, or mixtures thereof.

12. A test device according to claim 11, wherein said blocking agents are selected from the group consisting of proteinaceous blocking reagents which inhibit binding of molecules having a molecular weight of greater than about 1000 with said absorbent material and polymer blocking reagents which inhibit binding of molecules having a molecular weight of less than about 1000 with said absorbent material.

13. A test device according to claim 1, further comprising a reference electrode disposed on said absorbent material between said contact portion and said electrochemical measurement portion.

14. A test device according to claim 13, wherein said reference electrode is electrically connected to said first conductor and said second conductor.

15. A test device according to claim 13 or 3, wherein said reference electrode comprises silver, lead or mixtures thereof.

16. A test device according to claim 1 or 2, wherein either or both of said first conductor and said second conductor comprise one or more materials selected from the group consisting of platinum, gold, graphite, and silver.

17. A test device according to claim 1 or 2, wherein each of said first conductor and said second conductor comprise from 2 to 500 fingers.

18. A test device according to claim 1 or 2, wherein said fingers of said first and second conductors are each from about 1 $\mu$m to about 20 $\mu$m wide and are spaced from about 0.5 $\mu$m to about 10 $\mu$m apart.

19. A method for detecting or quantifying an analyte in a test sample, comprising:
   providing a test device comprising an absorbent material, said absorbent material comprising:
      a contact portion at or proximate to a first end of said absorbent material;
      an electrochemical measurement portion at a location on said absorbent material which is positioned away from the first end, wherein said electrochemical measurement portion comprises an electrochemical detector cell consisting of a first conductor comprising a plurality of fingers disposed on said absorbent material and a second conductor comprising a plurality of fingers disposed on said absorbent material, wherein said fingers of said first conductor are interdigitated with said fingers of said second conductor and wherein said first conductor and said second conductor are electrically connected to one another; and
      a liposome lysing portion segregated from said contact portion and having a liposome lysing agent bound thereto, wherein said liposome lysing portion either is positioned between said contact portion and said electrochemical measurement portion, or partially or completely coincides with said electrochemical measurement portion;
   combining a binding material specific for the analyte with a conjugate of an analyte analog and liposomes and the test sample in an electrolyte mixture, wherein said liposomes comprise an electroactive marker;
   incubating the mixture for a time sufficient to permit competition between any analyte present in the test sample and the conjugate for the binding material;
   contacting the mixture with said contact portion of said absorbent material after said incubating;
   applying a potential to said conductors, wherein said potential is sufficient to induce redox cycling of said marker;
   allowing the mixture to migrate from said contact portion through said electrochemical measurement portion of said absorbent material after said incubating, wherein migration of aggregates of conjugate and binding material formed during said incubating is inhibited by said absorbent material, and whereby said liposomes are lysed by said liposome lysing agent to release said marker, and said marker undergoes redox cycling induced by said conductors causing current to flow between said first and second conductors;
   detecting the presence or amount of said current; and
   correlating the presence or amount of said current with the presence or amount, respectively, of the analyte in the test sample.

20. A method according to claim 19, wherein the analyte analog is either the analyte or a reactive analog of the analyte.

21. A method according to claim 19, wherein said contacting is carried out by inserting the contact portion of the absorbent material into the mixture.

22. A method according to claim 19, wherein the contact portion further comprises a wicking portion at the first end, said contacting being carried out by spotting the mixture onto the absorbent material in the contact portion outside of the wicking zone, and said allowing comprises inserting the wicking portion into a wicking reagent.

23. A method according to claim 19, wherein said correlating is used to determine the amount of analyte in the test sample and is carried out by comparing the amount of the current flowing between the first and second conductors with one or more reference standards having known concentrations of the analyte for particular current amounts to determine the analyte concentration in the test sample relative to the known concentrations.

24. A method according to claim 19, wherein the liposomes are prepared from one or more phospholipids, glycolipids, steroids, alkyl phosphates, or fatty acid esters.

25. A method according to claim 19, wherein the analyte is an antigen or hapten, and the binding material is an antibody recognizing the antigen or the hapten.

26. A method according to claim 19, wherein said absorbent material further comprises a region for accumulation of aggregates formed from said conjugate and said binding material, wherein said region for accumulation is positioned away from said liposome lysing portion and either between said liposome lysing portion and said contact portion, or in said contact portion.

27. A method according to claim 19, wherein said test device further comprises a reference electrode disposed on said absorbent material between said contact portion and said electrochemical measurement portion, and wherein said reference electrode is electrically connected to said first conductor and said second conductor.

28. A method according to claim 27, wherein said reference electrode comprises silver, lead or mixtures thereof.

29. A method according to claim 19, wherein either or both of said first conductor and said second conductor comprise one or more materials selected from the group consisting of platinum, gold, graphite, and silver.

30. A method according to claim 19, wherein each of said first conductor and said second conductor comprise from 2 to 500 fingers.

31. A method according to claim 19, wherein said fingers of said first and second conductors are each from about 1 $\mu$m to about 20 $\mu$m wide and are spaced from about 0.5 $\mu$m to about 10 $\mu$m apart.

32. A method for detecting or quantifying an analyte in a test sample, comprising:
   providing a test device comprising an absorbent material, said absorbent material comprising:
      a contact portion at or proximate to a first end of said absorbent material;
      an electrochemical measurement portion at a location on said absorbent material which is positioned away from the first end, wherein said electrochemical measurement portion comprises an electrochemical detector cell consisting of a first conductor comprising a plurality of fingers disposed on said absorbent material and a second conductor comprising a plurality of fingers disposed on said absorbent material, wherein said fingers of said first conductor are interdigitated with said fingers of said second conductor and wherein said first conductor and said second conductor are electrically connected to one another;

a liposome lysing portion segregated from said contact portion and having a liposome lysing agent bound thereto, wherein said liposome lysing portion either is positioned between said contact portion and said electrochemical measurement portion, or partially or completely coincides with said electrochemical measurement portion; and a competitive binding portion positioned between and segregated from said contact and said liposome lysing portions on said absorbent material and having a binding material for the analyte bound to said competitive binding portion;

contacting an electrolytic mixture of the test sample and a conjugate of an analyte analog and liposomes with said contact portion of said absorbent material, wherein said liposomes comprise an electroactive marker;

applying a potential to said conductors, wherein said potential is sufficient to induce redox cycling of said marker;

allowing the mixture to migrate from said contact portion through said electrochemical measurement portion of said absorbent material, whereby said liposomes are lysed by said liposome lysing agent to release said marker, and said marker undergoes redox cycling induced by said conductors causing current to flow between said first and second conductors;

detecting the presence or amount of said current; and correlating the presence or amount of said current with the presence or amount, respectively, of the analyte in the test sample.

33. A method according to claim 32, wherein the analyte analog is either the analyte or a reactive analog of the analyte.

34. A method according to claim 32, wherein said contacting is carried out by inserting the contact portion of said absorbent material into said mixture.

35. A method according to claim 32, wherein said contact portion further comprises a wicking portion at the first end, said contacting is carried out by spotting said mixture onto said absorbent material in said contact portion outside of said wicking zone, and said allowing comprises inserting said wicking portion into a wicking reagent.

36. A method according to claim 32, wherein said correlating is used to determine the amount of analyte in the test sample and is carried out by comparing the amount of the current flowing between the first and second conductors with one or more reference standards having known concentrations of the analyte for particular current amounts to determine the analyte concentration in the test sample relative to the known concentrations.

37. A method according to claim 32, wherein said liposomes are prepared from one or more phospholipids, glycolipids, steroids, alkyl phosphates, or fatty acid esters.

38. A method according to claim 32, wherein said analyte is an antigen or hapten, and said binding material is an antibody for said antigen or said hapten.

39. A method according to claim 32, wherein said test device further comprises a reference electrode disposed on said absorbent material between said contact portion and said electrochemical measurement portion, and wherein said reference electrode is electrically connected to said first conductor and said second conductor.

40. A method according to claim 39, wherein said reference electrode comprises silver, lead or mixtures thereof.

41. A method according to claim 32, wherein either or both of said first conductor and said second conductor comprise one or more materials selected from the group consisting of platinum, gold, graphite, and silver.

42. A method according to claim 32, wherein each of said first conductor and said second conductor comprise from 2 to 500 fingers.

43. A method according to claim 32, wherein said fingers of said first and second conductors are each from about 1 $\mu$m to about 20 $\mu$m wide and are spaced from about 0.5 $\mu$m to about 10 $\mu$m apart.

* * * * *

UNITED STATES PATENT AND TRADEMARK OFFICE
CERTIFICATE OF CORRECTION

PATENT NO.   : 5,958,791   Page 1 of 1
DATED        : September 28, 1999
INVENTOR(S)  : Roberts et al.

It is certified that error appears in the above-identified patent and that said Letters Patent is hereby corrected as shown below:

<u>Title page,</u>
Item [75], Inventors, delete the following inventors: -- Richard A. Montagna and Geoffrey S. Rule --

Signed and Sealed this

Twenty-fifth Day of June, 2002

*Attest:*

*Attesting Officer*

JAMES E. ROGAN
*Director of the United States Patent and Trademark Office*

UNITED STATES PATENT AND TRADEMARK OFFICE
CERTIFICATE OF CORRECTION

| | | |
|---|---|---|
| PATENT NO. | : 5,958,791 | Page 1 of 1 |
| APPLICATION NO. | : 08/722901 | |
| DATED | : September 28, 1999 | |
| INVENTOR(S) | : Matthew A. Roberts | |

It is certified that error appears in the above-identified patent and that said Letters Patent is hereby corrected as shown below:

Col. 1 at lines 9-13, delete "This work was partially funded by the National Institutes of Health, DHHS, under the Superfund Basic Research and Education Program, NIEHS ES-05950. Fabrication of electrodes was performed at the National Nanofabrication Facility which is supported, in part, by the National Science Foundation under Grant No. ECS-8619049." and insert --This invention was made with government support under grant NIEHS ES-05950 awarded by National Institutes of Health, DHHS, under the Superfund Basic Research and Education Program and grant ECS-8619049 awarded by National Science Foundation. The government has certain rights in the invention-- in its place.

Signed and Sealed this

Twenty-fourth Day of February, 2009

JOHN DOLL
*Acting Director of the United States Patent and Trademark Office*